US012788286B2

(12) United States Patent
Assouad

(10) Patent No.: US 12,788,286 B2
(45) Date of Patent: Nov. 10, 2026

(54) OPTICAL DEVICE, SYSTEM AND METHOD FOR MONITORING BLOOD BORNE CHROMOPHORES

(71) Applicant: SPECTRONIX INC., Gatineau (CA)

(72) Inventor: Patrick Assouad, Ottawa (CA)

(73) Assignee: SPECTRONIX INC., Gatineau (CA)

( * ) Notice: Subject to any disclaimer, the term of this patent is extended or adjusted under 35 U.S.C. 154(b) by 434 days.

(21) Appl. No.: 18/031,864

(22) PCT Filed: Oct. 25, 2021

(86) PCT No.: PCT/CA2021/051500
§ 371 (c)(1),
(2) Date: Apr. 13, 2023

(87) PCT Pub. No.: WO2022/082323
PCT Pub. Date: Apr. 28, 2022

(65) Prior Publication Data

US 2023/0404443 A1 Dec. 21, 2023

Related U.S. Application Data

(60) Provisional application No. 63/232,587, filed on Aug. 12, 2021, provisional application No. 63/105,223, filed on Oct. 24, 2020.

(51) Int. Cl.
*A61B 5/1455* (2006.01)
*A61B 5/00* (2006.01)
(Continued)

(52) U.S. Cl.
CPC ........ *A61B 5/14551* (2013.01); *A61B 5/0075* (2013.01); *A61B 5/7282* (2013.01);
(Continued)

(58) Field of Classification Search
CPC .................................................... A61B 5/1455
See application file for complete search history.

(56) References Cited

U.S. PATENT DOCUMENTS 4,775,116 A 10/1988 Klein
5,315,995 A 5/1994 Rivers
(Continued)

FOREIGN PATENT DOCUMENTS

CA 3077122 10/2021
CA 3115419 10/2021
(Continued)

OTHER PUBLICATIONS

U.S. Appl. No. 17/046,704, filed May 10, 2019, Patrick Assouad.
(Continued)

*Primary Examiner* — Marjan Fardanesh
(74) *Attorney, Agent, or Firm* — Gray Ice Higdon

(57) ABSTRACT

Described herein are various embodiments of a broad spectrum optical device, system and method for monitoring blood-borne chromophores. In one embodiment, a system comprises a broad-spectrum light source to probe multiple blood-borne chromophores associated with a physiological condition; a spectrometer operable to acquire an optical signal resulting from the broad-spectrum illumination; and a digital data processor operable to process the broad-spectrum response to at least partially spectrally resolve respective spectral responses to output a health-related indicator.

20 Claims, 18 Drawing Sheets

(51) Int. Cl.
*A61H 31/00* (2006.01)
*A61M 16/00* (2006.01)
*A61M 16/04* (2006.01)

(52) U.S. Cl.
CPC .......... *A61B 5/746* (2013.01); *A61H 31/005* (2013.01); *A61M 16/0003* (2014.02); *A61M 16/0048* (2013.01); *A61M 16/04* (2013.01); *A61B 5/6803* (2013.01); *A61H 2230/201* (2013.01); *A61M 2202/0208* (2013.01)

(56) References Cited

U.S. PATENT DOCUMENTS

| | | | |
|---|---|---|---|
| 5,355,882 | A | 10/1994 | Ukawa et al. |
| 5,372,134 | A | 12/1994 | Richardson |
| 5,388,575 | A | 2/1995 | Taube |
| 5,457,284 | A | 10/1995 | Ferguson |
| 6,671,529 | B2 | 12/2003 | Claure et al. |
| 7,127,278 | B2 | 10/2006 | Melker et al. |
| 7,190,999 | B2 | 3/2007 | Geheb et al. |
| 8,712,493 | B2 | 4/2014 | Ukawa |
| 9,014,772 | B2 | 4/2015 | Yamaguchi et al. |
| 9,131,881 | B2 | 9/2015 | Diab et al. |
| 9,579,060 | B1 | 2/2017 | Lisy et al. |
| 9,775,546 | B2 | 10/2017 | Diab et al. |
| 10,531,819 | B2 | 1/2020 | Diab et al. |
| 10,660,551 | B2 | 5/2020 | Koyama et al. |
| 10,674,948 | B2 | 6/2020 | Diab et al. |
| 11,071,480 | B2 | 7/2021 | Diab et al. |
| 12,064,247 | B2 | 8/2024 | Everman et al. |
| 2002/0019587 | A1 | 2/2002 | Cheng et al. |
| 2003/0050541 | A1 | 3/2003 | Wuori |
| 2004/0267325 | A1 | 12/2004 | Geheb et al. |
| 2005/0070778 | A1 | 3/2005 | Lackey et al. |
| 2005/0228246 | A1 | 10/2005 | Lee et al. |
| 2006/0173258 | A1 | 8/2006 | Kobayashi et al. |
| 2007/0213964 | A1 | 9/2007 | Goldman |
| 2008/0139908 | A1 | 6/2008 | Kurth |
| 2008/0171311 | A1 | 7/2008 | Centen et al. |
| 2008/0200775 | A1 | 8/2008 | Lynn |
| 2008/0262327 | A1 | 10/2008 | Kato |
| 2008/0269589 | A1 | 10/2008 | Thijs et al. |
| 2008/0306337 | A1 | 12/2008 | Livingston et al. |
| 2010/0076319 | A1 | 3/2010 | Mannheimer et al. |
| 2011/0218409 | A1 | 9/2011 | Kugler et al. |
| 2011/0245711 | A1 | 10/2011 | Katra et al. |
| 2012/0065486 | A1 | 3/2012 | Imran |
| 2013/0281803 | A1 | 10/2013 | Scheele et al. |
| 2014/0012144 | A1 | 1/2014 | Crone |
| 2014/0100788 | A1 | 4/2014 | Heikkinen et al. |
| 2015/0254414 | A1 | 9/2015 | Patel |
| 2017/0071550 | A1 | 3/2017 | Newberry |
| 2017/0112422 | A1 | 4/2017 | Hatch |
| 2017/0119254 | A1 | 5/2017 | Ando et al. |
| 2017/0224220 | A1 | 8/2017 | Tunnell et al. |
| 2017/0325784 | A1 | 11/2017 | Friedrich et al. |
| 2018/0001980 | A1 | 1/2018 | Hulbert |
| 2018/0207058 | A1 | 7/2018 | Xu et al. |
| 2018/0310822 | A1 | 11/2018 | Indorf et al. |
| 2019/0290194 | A1 | 9/2019 | Umekawa et al. |
| 2020/0310098 | A1 | 10/2020 | Ince et al. |

FOREIGN PATENT DOCUMENTS

| | | |
|---|---|---|
| CN | 1245407 | 2/2000 |
| CN | 1326328 | 12/2001 |
| CN | 103203013 | 7/2013 |
| EP | 1304955 | 5/2003 |
| EP | 2075189 | 7/2009 |
| JP | H05124592 | 5/1993 |
| JP | 1993207993 | 11/2000 |
| JP | 3116252 | 12/2000 |
| JP | 2008534083 | 8/2008 |
| JP | 2009501041 | 1/2009 |
| JP | 2018536516 | 12/2018 |
| JP | 2019502418 | 1/2019 |
| WO | 2007080303 | 7/2007 |
| WO | 2008013506 | 1/2008 |
| WO | 2009022926 | 2/2009 |
| WO | 2010129528 | 11/2010 |
| WO | 2013165887 | 11/2013 |
| WO | 2017078637 | 5/2017 |
| WO | 2019081547 | 5/2019 |
| WO | 2019213783 | 11/2019 |
| WO | 2022082322 | 4/2022 |
| WO | 2022082323 | 4/2022 |

OTHER PUBLICATIONS

U.S. Appl. No. 63/105,223, filed Oct. 24, 2020, Patrick Assouad.

U.S. Appl. No. 63/125,367, filed Dec. 14, 2020, Patrick Assouad.

Bein et al. Monitoring of cerebral oxygenation with near infrared spectroscopy and tissue oxygen partial pressure during cardiopulmonary resuscitation in pigs. European Journal of Anaesthesiology 2006; 23: 501-509.

Callaway. Cerebral Oximetry and Cardiopulmonary Resuscitation. Journal of the American Heart Association. Jul. 28, 2021. pp. 1-2.

Chien et al. Cerebral Oxygenation During Hypoxia and Resuscitation by Using Near-infrared Spectroscopy in Newborn Piglets. ChinMedAssoc • Feb. 2007 • vol. 70 • No. 2. pp. 47-55.

Genbrugge et al.Regional Cerebral Oximetry During Cardiopulmonary Resuscitation: Useful Or Useless? The Journal of Emergency Medicine, vol. 50, No. 1, pp. 198-207, 2016.

Green et al. Cerebral oximetry and its role in adult cardiac, non-cardiac surgeryand resuscitation from cardiac arrest. Anaesthesia 2017, 72 (Suppl. 1), 48-57.

Hanning CD, Alexander-Williams JM. Pulse oximetry: a practical review. BMJ. 1995;311(7001):367-370. doi:10.1136/bmj.311.7001.367.

Hirose et al. Pre-hospital portable monitoring of cerebral regional oxygen saturation (rSO2) in seven patients with out-of-hospital cardiac arrest. BMC Res Notes (2016) 9:428 pp. 1-5.

Ibrahim et al. Cerebral Oximetry as a Real-Time Monitoring Tool to Assess Quality ofIn-Hospital Cardiopulmonary Resuscitation and Post Cardiac Arrest Care. Journal of the American Heart Association. Jul. 28, 2021. pp. 1-5.

Jones, et al., Underwater near-infrared spectroscopy measurements of muscle oxygenation: laboratory validation and preliminary observations in swimmers and triathletes, Journal of Biomedical Optics 19(12), Dec. 2014.

Larsson A., Uusijärvi J., Eksborg S., "Tissue oxygenation measured with near-infrared spectroscopy during normobaric and hyperbaric oxygen breathing in healthy subjects", European Journal of Applied Physiology, 2010, pp. 757-761, vol. 109, Springer.

Larsson et al. Tissue oxygenation measured with near-infrared spectroscopy during normobaric and hyperbaric oxygen breathing in healthy subjects, Eur J Appl Physiol (2010) 109:757-761, Feb. 10, 2020, pp. 757 to 761.

Litscher et al., Transcranial Cerebral Oximetry in the Hyperbaric Environment, Department of Anesthesiology and Intensive Care Medicine, Biomed, Technik, 42 (1997) p. 38.

Litscher G., Schwarz G., Ratzenhofer-Komenda B., Kovacs H., Gabor S., Stolle-Jüttner F. M., "Transcranial Cerebral Oximetry in the Hyperbaric Environment", Biomedizinische Technik, 1997, pp. 38-41, vol. 42.

Masimo, Oxygen Reserve Index (ORi), Whitepaper, 2017.

Mcleod et al., Measuring Cerebral Oxygenation During Normobaric Hyperoxia: A Comparison of Tissue Microprobes, Near-Infrared Spectroscopy, and Jugular Venous Oximetry in Head Injury, Departments of *Neuroanaesthesia and †Medical Physics & Bioengineering, The National Hospital for Neurology and Neurosurgery, University College London Hospitals & Centre for Anaesthesia, Anesth Analg 2003; 97:851-856).

Meter—Hyperbaric Oxygen in Resuscitation. Springer International Publishing AG 2017K.K. Jain, Textbook of Hyperbaric Medicine. 551-566.

(56) References Cited

OTHER PUBLICATIONS

Olafsdottir OB, Eliasdottir TS, Kristjansdottir JV, Hardarson SH, Stefansson E (2015) "Retinal Vessel Oxygen Saturation during 100% Oxygen Breathing in Healthy Individuals." PLoS One 10(6): e0128780. doi:10.1371/journal.pone.0128780.

Parnia et al. Cerebral Oximetry During Cardiac Arrest: A Multicenter Study of Neurologic Outcomes and Survival. pp. 1-27.

Parnia. Cerebral oximetry—The holy grail of non-invasive cerebral perfusion monitoring in cardiac arrest or just a false dawn? Editorial / Resuscitation 83 (2012) 11-12. Oct. 27, 2011.

Patterson, et al., Time resolved reflectance and transmittance for the non-invasive measurement of tissue optical properties, Applied Optics, vol. 28, No. 12, Jun. 15, 1989 (p. 2331-2336).

Price et al. Response to Use of Cerebral Oximetry During Cardiac Arrest. Online Letters to the Editor. Mar. 2017, vol. 45, No. 3. e334-e335.

Putzer et al. Monitoring of brain oxygenation during hypothermic CPR—A prospective porcine study. Resuscitation 104 (2016) pp. 1-5.

Sanfilippoa et al. "Cerebral oximetry and return of spontaneous circulation after cardiac arrest: A systematic review and meta-analysis". Elsevier. Resuscitation 94 (2015) 67-72.

Suzuki, et al., A Tissue Oxygenation Monitor using NIR Spatially Resolved Spectroscopy, Proceedings of Optical Tomography and Spectroscopy of Tissue III, San Jose, California, SPIE vol. 2597, Jan. 1999.

Taccone. Cerebral oximetry during extracorporeal cardiopulmonary resuscitation. Critical Care 2013, 17:409 pp. 1-2.

Tajima et al. "Portable system for monitoring of regional cerebral oxygen saturation during prehospital cardiopulmonary resuscitation: a pilot study". Brief Communication. Acute Medicine & Surgery 2015; 2: 48-52.

Takegawa et al. Near-Infrared Spectroscopy Assessments of Regional CerebralOxygen Saturation for the Prediction of Clinical Outcomes in Patients WithCardiac Arrest: A Review of Clinical Impact, Evolution, and Future Directions. Frontiers in Medicine. Published: Oct. 29, 2020.

International Search Report and Written Opinion issued in Application No. PCT/CA2021/051500, 15 pages, dated Jan. 27, 2022.

China National Intellectual Property Administration: First Office Action issued for Application No. 202180087216.4, 28 pages, dated Dec. 3, 2025.

OPTICAL DEVICE, SYSTEM AND METHOD FOR MONITORING BLOOD BORNE CHROMOPHORES

CROSS REFERENCE TO RELATED APPLICATIONS

This application claims priority to U.S. Provisional Application No. 63/105,223 filed Oct. 24, 2020, and to U.S. Provisional Application No. 63/232,587 filed Aug. 12, 2021, the entire disclosure of each of which is incorporated herein by reference.

FIELD OF THE DISCLOSURE

The present disclosure relates to optical medical devices, and, in particular, to an optical device, system and method for monitoring blood-borne chromophores.

BACKGROUND

Pulse oximetry is often used in health-related systems to monitor blood oxygenation. This typically works by emitting near-infrared (NIR) light into tissues, measuring the corresponding transmitted or reflected light at two distinct wavelengths, typically for oxyhemoglobin and/or deoxyhemoglobin, and deriving from changes in absorbance a corresponding change in concentration of oxyhemoglobin and/or deoxyhemoglobin, for instance, in the form of an estimate from relative variations, calibration or via index-tables. Various devices rely on pulse oximetry to notify users or healthcare professionals of blood concentration abnormalities detected.

It is known that the accuracy of pulse oximetry is affected by several factors, including poor circulation, skin pigmentation, skin thickness, skin temperature, current tobacco use, and use of fingernail polish, for example. On Feb. 19, 2021, the Federal Drug Association (FDA) released a Safety Communication entitled "Pulse Oximeter Accuracy and Limitations: FDA Safety Communication" which warned healthcare practitioners of these confounding factors and indicated that pulse oximeters are least accurate when oxygen saturations are less that 80%. The FDA concluded that pulse oximeters should be recognised as providing only an estimate of blood oxygen saturation, with at least a 4% variance.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for an optical device, system and method for monitoring blood-borne chromophores that overcome known technologies, or at least, provides a useful alternative thereto.

In accordance with one aspect, there is provided a system for interfacing with a user body region to monitor a physiological condition, the system comprising: a broad-spectrum light source providing broad-spectrum illumination to the user body region within a designated spectral region to probe multiple blood-borne chromophores associated with the physiological condition and exhibiting respective spectral responses within the designated spectral region; a spectrometer operable to acquire an optical signal from the user body region resulting from the broad-spectrum illumination so to digitally capture a broad-spectrum response encompassing the respective spectral responses; and a digital data processor operable to process the broad-spectrum response to at least partially spectrally resolve the respective spectral responses to output a health-related indicator associated with the blood-borne chromophores and representative of the physiological condition.

In one embodiment, the physiological condition comprises a physiological event, and the digital data processor is operable to process the broad-spectrum response in real time so to output a temporally variable health-related indicator that temporally resolves the physiological event.

In one embodiment, the physiological event comprises oxygen delivery associated with an oxygen bolus externally administered to a user, the blood-borne chromophores comprise at least one blood-oxygenation-related chromophore, and the digital data processor is operable to temporally resolve the oxygen delivery associated with the oxygen bolus to the user body region.

In one embodiment, the oxygen bolus is administered via any one of intubation of the user, or administration of cardiopulmonary resuscitation (CPR) to the user.

In one embodiment, the physiological event comprises sequential oxygen delivery associated with sequential oxygen boluses externally administered to a user, the blood-borne chromophores comprise at least one blood-oxygenation-related chromophore, and the digital data processor is operable to temporally resolve each of the sequential oxygen delivery associated with each of the sequential oxygen boluses.

In one embodiment, the digital data processor is further operable to process the temporally resolved oxygen delivery to output an indicator of oxygen delivery efficacy in guiding administration of subsequent oxygen boluses.

In one embodiment, the digital data processor is further operable to determine an oxygen transport delay based on an elapsed time between receiving notification of administration of the oxygen bolus and identifying an oxygen delivery variation temporally associated therewith in the broad-spectrum response.

In one embodiment, the digital data processor is further operable to spectrally resolve the respective spectral responses to isolate a spectral signature for at least one of the blood-borne chromophores and compare the signature with a designated signature associated with a discriminable physiological condition to output the health-related indicator.

In one embodiment, the digital data processor is further operable to spectrally resolve the respective spectral responses to isolate a spectral signature for at least one of the blood-borne chromophores, and the digital data processor is operable to extract an absolute concentration for the at least one of the blood-borne chromophores from the spectral signature.

In one embodiment, the digital data processor is operable to: compare a combined spectral signature associated with the blood-borne chromophores and compare the combined spectral signature with a designated set of corresponding signatures to characterize an extent of the physiological condition via the health-related indicator.

In one embodiment, the digital data processor is operable to extract a variation in the spectral signature over time and compare the variation with the designated signature to output the health-related indicator.

In one embodiment, the broad-spectrum light source comprises a full spectrum infrared (IR) light source.

In one embodiment, the broad-spectrum light source emits light in a range of about 600 nm to about 1000 nm.

In one embodiment, the spectrometer is operable to isolate respective spectral responses within at least 10 spectral regions within the broad-spectrum illumination.

In one embodiment, the spectrometer is operable to isolate respective spectral responses within at least 40 spectral regions within the broad-spectrum illumination.

In one embodiment, the spectrometer is operable to isolate respective spectral responses within at least 80 spectral regions within the broad-spectrum illumination.

In one embodiment, the digital data processor is operable to identify overlapping respective spectral responses in the optical signal by deconstructing the optical signal via spectral deconvolution.

In one embodiment, the user body region comprises a cerebral region.

In one embodiment, the broad-spectrum light source and spectrometer are integrated within a headband.

In one embodiment, the digital data processor is operable to output a time-variable integrated response amplitude, and the temporal variations of the respective spectral responses are reflected as temporally corresponding features in the time-variable integrated response amplitude.

In one embodiment, the digital data processor is operable to derive from the time-variable integrated response amplitude a temporal index representative of the respective spectral responses.

In one embodiment, the temporal index has a resolution sufficient to observe the temporal variations in the respective spectral responses corresponding to discrete physiological events over time.

In one embodiment, the digital data processor is operable to process the optical signal such that the temporal variations in the output are identifiable within seconds of discrete physiological events.

In one embodiment, the system is operable in the absence of a detectable pulse at the user body region.

In one embodiment, the blood-borne chromophores comprise any one or more of: oxyhemoglobin, deoxyhemoglobin, oxymyoglobin, deoxymyoglobin, dissolved oxygen, carbon monoxide, melanin, cytochrome oxidase, or water.

In one embodiment, the physiological condition comprises any one or combination of: blood or tissue oxygenation, pulse, blood pressure, blood volume, blood flow rate, blood loss or hemorrhaging, onset of blackouts or change in cognition, lung efficiency, oxygen delivery, rate of oxygen consumption by an organ of interest, psychological or physiological stress, presence of stroke, a change in vital signs, or hydration or dehydration.

In one embodiment, the system is configured to monitor oxygenation levels at the user body region over time.

In one embodiment, the system is configured to monitor blood volume variations at the user body region.

In one embodiment, the blood-borne chromophores comprise water molecules and the system is configured to monitor hydration levels at the user body region based on temporal variations of the water molecules.

In one embodiment, the digital data processer is operable to store the broad-spectrum response on a memory to configure a user-specific spectral index.

In one embodiment, the digital data processor is operable to compare the broad-spectrum response with any one or both of: a user-specific spectral index, or a user-agnostic spectral index.

In one embodiment, the digital data processor is operable to predict a user outcome based on temporal variations and any one or both of: a user-specific spectral index, or a user-agnostic spectral index.

In one embodiment, the probe is provided as a wearable oximeter device.

In one embodiment, the system comprises an additional light source and spectrometer fixable in respect of a distinct user body region and in operative communication with the digital data processor such that the digital data processor monitors the physiological condition via each of the body regions.

In one embodiment, the physiological condition comprises oxygen delivery to the user body region, the blood-borne chromophores comprise at least one blood-oxygenation-related chromophore, the digital data processor is operable to digitally resolve oxygen delivery variations over time based on variations in the at least one blood-oxygenation-related chromophore to digitally identify any one of: an oxygen concentration increase, an oxygen concentration decrease, or a relatively unchanged oxygen concentration, which is temporally associated with one or more physiological events experienced by the user.

In one embodiment, the one or more physiological events resulting in the oxygen concentration increase comprises any one or combination of: inhalation by the user; intubation of the user; or mechanical administration of cardiopulmonary resuscitation (CPR) to the user.

In one embodiment, the one or more physiological events resulting in the oxygen concentration decrease comprises any one or combination of: an obstructed airway of the user; sleep apnea of the user; or cardiac arrest of the user.

In accordance with another aspect, there is provided an oximeter for monitoring a physiological condition, the oximeter comprising: a broad-spectrum light source for providing broad-spectrum illumination to a user body region in probing multiple blood-related chromophores exhibiting distinguishable spectral responses; and a spectrometer operable to acquire an optical signal from the user body region resulting from the broad-spectrum illumination so to digitally capture the distinguishable spectral responses.

In one embodiment, the broad-spectrum light source comprises a broadband infrared (IR) light source.

In one embodiment, the broadband light source emits light in a range of about 600 nm to about 1000 nm.

In one embodiment, the spectrometer is operable to isolate respective spectral responses within at least 10 spectral regions within the broadband illumination.

In one embodiment, the spectrometer is operable to isolate respective spectral responses within at least 40 spectral regions within the broadband illumination.

In one embodiment, the spectrometer is operable to isolate respective spectral responses within at least 80 spectral regions within the broadband illumination.

In one embodiment, the oximeter is integrated within a headband.

In accordance with another aspect, there is provided an oximetry system for temporally monitoring oxygen levels at a user body region in real time, the system comprising: a light source providing illumination to the user body region within a designated spectral region to probe various blood-borne chromophores exhibiting respective spectral responses within the designated spectral region, at least one of the chromophores comprising a blood-oxygenation-related chromophore; a spectrometer operable to acquire an optical signal from the user body region resulting from the illumination so to digitally capture a response encompassing the respective spectral responses; and a digital data processor operable to process the response to automatically resolve a temporally-defined oxygen delivery event at the user body region in real time.

In one embodiment, the oxygen delivery event corresponds to an oxygen bolus externally administered to the user, and the digital data processor is operable to temporally resolve the oxygen delivery associated with the bolus to the user body region.

In one embodiment, the oxygen bolus is administered via any one of intubation of the user, or administration of cardiopulmonary resuscitation (CPR) to the user.

In one embodiment, the temporally-defined oxygen delivery event comprises sequential oxygen deliveries associated with sequential oxygen boluses externally administered to the user, and the digital data processor is operable to temporally resolve each of the sequential oxygen deliveries associated with each of the boluses.

In one embodiment, the digital data processor is further operable to process the temporally resolved oxygen delivery to output an indicator of oxygen delivery efficacy in guiding administration of subsequent oxygen boluses.

In one embodiment, the digital data processor is operable to resolve the temporally-defined oxygen delivery event within seconds.

In one embodiment, the digital data processor is further operable to determine an oxygen transport delay based on an elapsed time between receiving notification of administration of the oxygen bolus and identification of the temporally-defined oxygen delivery event at the user body region.

In accordance with yet another aspect, there is provided non-transitory computer-readable medium comprising instructions to be implemented by one or more digital data processors to monitor a physiological condition at a user body region, by: activating a broad-spectrum light source providing broad-spectrum illumination within a designated spectral region to the user body region to probe multiple blood-borne chromophores associated with the physiological condition and exhibiting respective spectral responses within the designated spectral region; acquiring from a spectrometer an optical signal from the user body region resulting from the broad-spectrum illumination so as to digitally capture a broad-spectrum response encompassing the respective spectral responses; and processing the broad-spectrum response to at least partially spectrally resolve the respective spectral responses to output a health-related indicator associated with the blood-borne chromophores and representative of the physiological condition.

In one embodiment, the physiological condition comprises a physiological event, and the processing comprises processing the broad-spectrum response in real time so as to output a temporally variable health-related indicator that temporally resolves the physiological event.

In one embodiment, the physiological event comprises oxygen delivery associated with an oxygen bolus externally administered to a user, the blood-borne chromophores comprise at least one blood-oxygenation-related chromophore, and the processing comprises processing the broad-spectrum response so as to temporally resolve the oxygen delivery associated with the oxygen bolus to the user body region.

In one embodiment, the oxygen bolus is administered via any one of intubation of the user, or administration of cardiopulmonary resuscitation (CPR) to the user.

In one embodiment, the physiological event comprises sequential oxygen delivery associated with sequential oxygen boluses externally administered to a user, the blood-borne chromophores comprise at least one blood-oxygenation-related chromophore, and the processing comprises processing the broad-spectrum response so as to temporally resolve each of the sequential oxygen delivery associated with each of the sequential oxygen boluses.

In one embodiment, the processing further comprises processing the temporally resolved oxygen delivery to output an indicator of oxygen delivery efficacy in guiding administration of subsequent oxygen boluses.

In one embodiment, the instructions further comprise determining an oxygen transport delay based on an elapsed time between receiving notification of administration of the oxygen bolus and identifying an oxygen delivery variation temporally associated therewith in the broad-spectrum response.

In one embodiment, the processing comprises isolating a spectral signature for at least one of the blood-borne chromophores and comparing the spectral signature with a designated signature associated with a di scriminable physiological condition to output the health-related indicator.

In one embodiment, the processing comprises isolating a spectral signature for at least one of the blood-borne chromophores and extracting an absolute concentration for the at least one of the blood-borne chromophores from the spectral signature.

In one embodiment, the processing comprises isolating a combined spectral signature associated with the blood-borne chromophores and comparing the combined spectral signature with a designated set of corresponding signatures to characterize an extent of the physiological condition via the health-related indicator.

In one embodiment, the processing further comprises extracting a variation in the spectral signature or the combined spectral signature, respectively, over time and comparing the variation with the designated signature or the designated set of corresponding signatures, respectively to output the health-related indicator.

In one embodiment, the broad-spectrum light source comprises a full spectrum infrared (IR) light source.

In one embodiment, the broad-spectrum light source emits light in a range of about 600 nm to about 1000 nm.

In one embodiment, the spectrometer is operable to isolate respective spectral responses within at least 10, 40, or 80, spectral regions within the broad-spectrum illumination.

In one embodiment, the processing further comprises identifying overlapping respective spectral responses in the optical signal by deconstructing the optical signal via spectral deconvolution.

In one embodiment, the user body region comprises a cerebral region, and the broad-spectrum light source and spectrometer are integrated within a headband.

In one embodiment, the instructions include outputting a time-variable integrated response amplitude, and temporal variations of the respective spectral responses are reflected as temporally corresponding features in the time-variable integrated response amplitude.

In one embodiment, the instructions include deriving from the time-variable integrated response amplitude a temporal index representative of the respective spectral responses.

In one embodiment, the temporal index has a resolution sufficient to observe the temporal variations in the respective spectral responses corresponding to discrete physiological events over time.

In one embodiment, the temporal variations are identifiable within seconds of discrete physiological events.

In one embodiment, the health-related indicator associated is outputted in the absence of a detectable pulse at the user body region.

In one embodiment, the blood-borne chromophores comprise any one or more of: oxyhemoglobin, deoxyhemoglobin, oxymyoglobin, deoxymyoglobin, dissolved oxygen, carbon monoxide, melanin, cytochrome oxidase, or water.

In one embodiment, the physiological condition comprises any one or combination of: blood or tissue oxygenation, pulse, blood pressure, blood volume, blood flow rate, blood loss or hemorrhaging, onset of blackouts or change in cognition, lung efficiency, oxygen delivery, rate of oxygen consumption by an organ of interest, psychological or physiological stress, presence of stroke, a change in vital signs, or hydration or dehydration.

In one embodiment, the instructions are configured to monitor oxygenation levels at the user body region over time.

In one embodiment, the instructions are configured to monitor blood volume variations at the user body region.

In one embodiment, the blood-borne chromophores comprise water molecules and the instructions are configured to monitor hydration levels at the user body region based on temporal variations of the water molecules.

In one embodiment, the instructions further comprise storing the broad-spectrum response on a memory to configure a user-specific spectral index.

In one embodiment, the instructions further comprise comparing the broad-spectrum response with any one or both of: a user-specific spectral index, or a user-agnostic spectral index.

In one embodiment, the instructions further comprise predicting a user outcome based on temporal variations and any one or both of: a user-specific spectral index, or a user-agnostic spectral index.

In one embodiment, the broad-spectrum light source and the spectrometer are provided as a wearable oximeter device.

In one embodiment, the non-transitory computer-readable medium further comprises instructions to be implemented by the one or more digital data processors to monitor the physiological condition at a second user body region, by: activating a second broad-spectrum light source providing the broad-spectrum illumination within the designated spectral region to the second user body region to probe the multiple blood-borne chromophores; acquiring from a second spectrometer a second optical signal from the second user body region resulting from the broad-spectrum illumination so as to digitally capture a second broad-spectrum response encompassing the respective spectral responses; and processing the second broad-spectrum response to at least partially spectrally resolve the respective spectral responses to output a second health-related indicator associated with the blood-borne chromophores and representative of the physiological condition at the second user body region.

In one embodiment, the physiological condition comprises oxygen delivery to the user body region, the blood-borne chromophores comprise at least one blood-oxygenation-related chromophore, the processing comprises digitally resolving oxygen delivery variations over time based on variations in the at least one blood-oxygenation-related chromophore to digitally identify any one of: an oxygen concentration increase, an oxygen concentration decrease, or a relatively unchanged oxygen concentration, which is temporally associated with one or more physiological events experienced by a user.

In one embodiment, the one or more physiological events resulting in the oxygen concentration increase comprises any one or combination of: inhalation by the user; intubation of the user; or mechanical administration of cardiopulmonary resuscitation (CPR) to the user.

In one embodiment, the one or more physiological events resulting in the oxygen concentration decrease comprises any one or combination of: an obstructed airway of the user; sleep apnea of the user; or cardiac arrest of the user.

In one embodiment, the instructions are executable in real-time to provide real-time monitoring of the physiological condition.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein.

Figure 1:
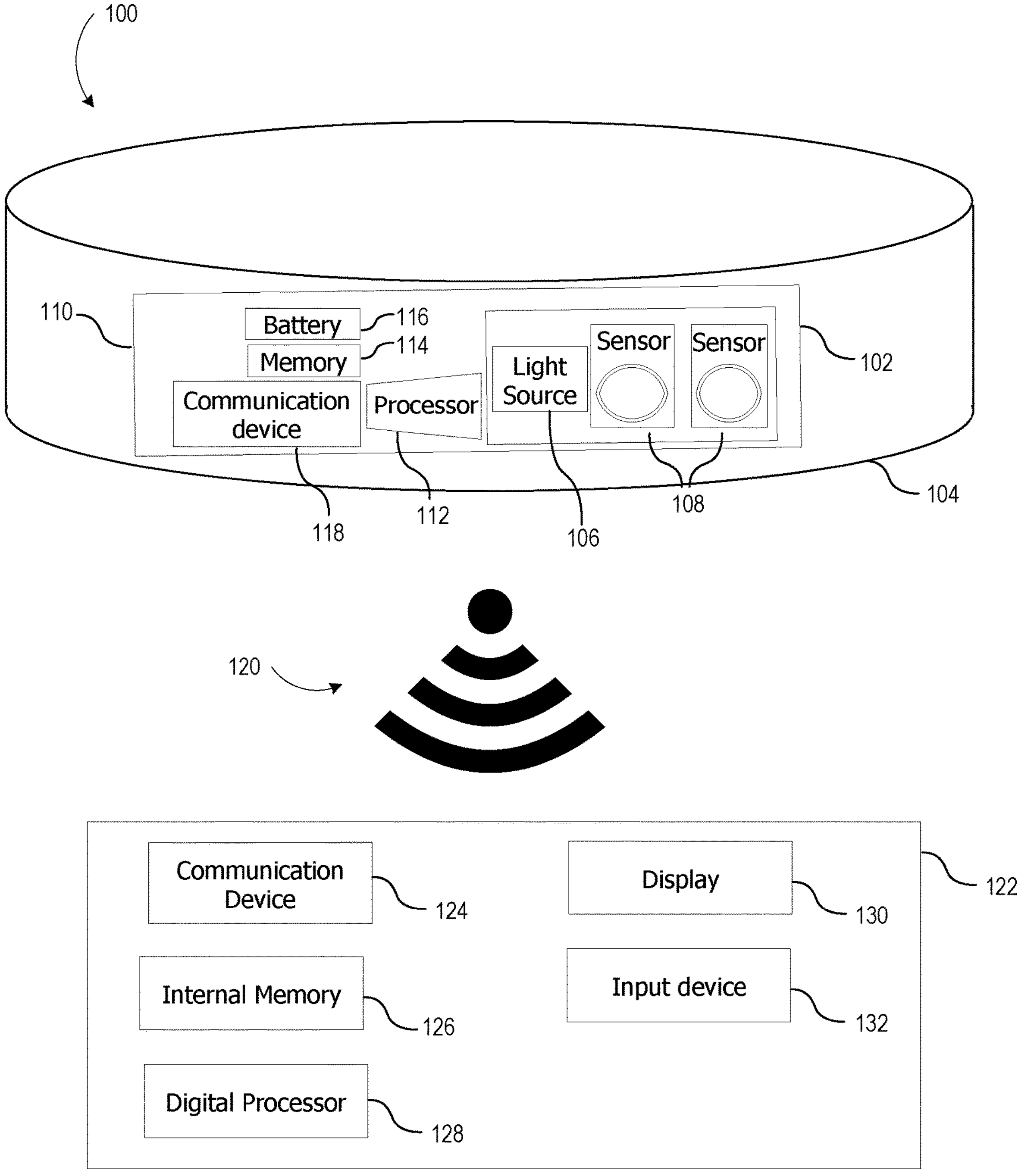
FIG. 1 is a schematic diagram of a broad or full spectrum oximetry (spectroximetry) system, in accordance with one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Unless defined otherwise, all technical and scientific terms used herein have the same meaning as commonly understood by one of ordinary skill in the art to which the present disclosure belongs.

Throughout the specification and claims, the following terms take the meanings explicitly associated herein, unless the context clearly dictates otherwise. The phrase "in one of the embodiments" or "in at least one of the various embodiments" as used herein does not necessarily refer to the same embodiment, though it may. Furthermore, the phrase "in another embodiment" or "in some embodiments" as used herein does not necessarily refer to a different embodiment, although it may. Thus, as described below, various embodiments may be readily combined, without departing from the scope or spirit of the innovations disclosed herein.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification and claims, the meaning of singular forms "a," "an," and "the" include plural references unless the context clearly dictates otherwise. The meaning of "in" includes "in" and "on."

The term "comprising" as used herein will be understood to mean that the list following is non-exhaustive and may or may not include any other additional suitable items, for example one or more further feature(s), component(s) and/or element(s) as appropriate.

The systems and methods described herein provide, in accordance with different embodiments, different examples of a system, method and related non-transitory computer medium, for monitoring or assessing one or more physiological or health-related parameters or condition(s) in a user or patient via spectrometry and in particular, in some embodiments, oximetry, or full or broad-spectrum oximetry, which is herein interchangeably referred to as spectroximetry or hyperspectral oximetry. Indeed, the various embodiments described herein contemplate different approaches and solutions for monitoring blood-borne chromophores in monitoring for different physiological conditions and/or physiological events.

For example, in some embodiments, oximetric solutions as described herein can provide for the effective temporal monitoring of oxygen levels at a user body region in real time, for example, in resolving observation of individual physiological events in real time. For example, physiological events manifesting oxygen concentration increases observable using the techniques described herein may include, but are not limited to, inhalation by a user, intubation of a user, or again mechanical administration of cardiopulmonary resuscitation (CPR) to a user, to name a few examples. Using broad-spectrum oximetry, or improvements in processing of two-wavelength oximetry, such temporal events may be resolved and observed, for different purposes or applications. As a result, such observations may lead to identification and monitoring of oxygen transport to the user body region under monitoring, improvements in the delivery or methods of delivery of oxygen to this region, diagnostics or screenings associated with any delayed, obstructed or interfered delivery, or the like. Other temporal or regional oxygen transport, delivery, accumulation or variation assessments, screenings, diagnostics, or procedure feedback may be considered, as will be detailed in a non-limiting manner, in the following description.

Similarly, other blood-borne chromophores may be independently or concurrently monitored using embodiments of the devices, systems and methods as described herein to monitor, for example, different physiological conditions, such dehydration, or the like, as further detailed below. Indeed, the provision of a broad-spectrum probe to extract a broad-spectrum reading of blood-borne chromophores may allow for the monitoring not only of specific absorption peaks, as may be more commonly contemplated using standard oximeters, but rather, to observe and monitor a broad-spectrum response to the probe in monitoring spectral profile variations or signatures indicative of relative or absolute variations in blood-borne chromophore concentrations indicative of one or more physiological conditions or events.

As noted above, conventional oximetry typically relies on measurement ratios for two blood-oxygen-related absorption wavelengths/peaks (oxyhemoglobin and deoxyhemoglobin) to produce useable, but limited results. Indeed, absorption ratios lose specificity in observing actual or absolute blood oxygen concentrations and neglect the finer detail otherwise available using techniques as described herein that probe and analyze greater portions of the blood or probe tissue's absorption spectrum. Moreover, since conventional oximetry devices rely on indices that are derived principally as ratios and are relative to baseline measurements, conventional oximetry also requires calibration (or the use of look-up tables) to associate a measured index with a saturation level, further restricting use and applicability. Furthermore, conventional pulse oximeters often do not provide reliable readings when saturation is low, and require that a pulse or heart beat be continuously and accurately detectable. While spatially-resolved spectrometry can provide further information as it invokes a spatial investigation, it remains constrained to the analysis of relative spatially-resolved concentration ratios, and thus remains unable to extract absolute total concentrations. Furthermore, the discrete measurements of two wavelengths taken by conventional oximeters unavoidably results in devices which fail to isolate spectral peak shifts. For example, where a conventional medical spectrometry device may be operated to probe the patient's blood at a specific wavelength where an absorption peak is anticipated, such devices will not allow for the observation of an unexpected peak shift, for example, which would effectively be measured as a signal reduction, rather than to observe the actual peak's shift to a slightly different wavelength, observable in the herein-described embodiments as a spectral profile variation carrying greater wealth of extractable information.

In contrast, full or broad-spectrum oximetry (spectroximetry or hyperspectral oximetry), as provided by the various systems and methods described below, in accordance with different embodiments, has the unique feature of allowing the measurement of the entire absorption spectrum of interest, such as for example between 600 nm and 1000 nm. Namely, a broad range of probing wavelengths can be leveraged, in different embodiments, to extract a coarse or even fine resolution absorption spectrum that carries a greater wealth of information for the purposes of conducing and outputting a more detailed analysis and evaluation of the probed tissue's oxygenation profile, status or condition.

For instance, in some embodiments, spectroximetry has the advantage of measuring absolute energetic transmission over a broad range of wavelength. This absolute measurement can allow for the comparison of absorption profile variations for the same patient at different times, and between patients, for example. Current oximetry methodologies rely on indices that do not lend to such analysis.

Furthermore, by monitoring a broad range of wavelengths, spectroximetry allows absorption peak shifts to be readily detected.

In the embodiments described below, spectroximetry is described with reference to a broad range of wavelengths in the near-IR and IR range of 600 nm to 1000 nm. It is to be appreciated that in this context, the term "broad range" is not intended to imply a continuous range (although it may be). Instead, "broad range" refers generally to a broad collection of wavelengths or wavelength regions across a range. Such wavelengths or wavelength regions may present a continuous, discontinuous or quasi-continuous spectrum within the range of 600 nm to 1000 nm. The wavelengths or wavelength regions within the range of 600 nm to 1000 nm may be selected for particular spectral solutions or applications, as will be readily understood below, and different wavelengths or wavelength regions may be associated with different spectral profiles or solutions. Therefore, while continuous broad-spectrum oximetry is considered herein, in some embodiments, other embodiments may rely on alternative measures and processing techniques for distinct wavelengths or spectral regions, to achieve similar effects in the observation of physiological events over time.

The embodiments of the present disclosure described below may further address the user-specific accuracy issues of conventional pulse oximetry, by the broad-spectrum solution compensating for confounding factors such as poor circulation, skin pigmentation, skin thickness, skin temperature, current tobacco use, inter alia.

With reference to FIG. 1, and in accordance with one exemplary embodiment, a full spectrum oximetry system, interchangeably referred to as a spectroximetry system, and generally referred to using the numeral 100, will now be described.

In this exemplary embodiment, system 100 comprises a broad-spectrum probe 102, which may be attached to the skin above the tissue of interest or as illustrated herein integrated into or inside a type of headwear (here headband 104). Probe 102 generally comprises at least one broad-spectrum infrared light source 106, for example one or more light emitting diodes (LEDs) may be used alone or in combination to generate infrared (IR) light covering a broad range of the infrared spectrum (e.g. for example wavelengths between 600 nm to 1000 nm). Light source 106 is generally configured so as to emit light into the tissue of interest, this example the head/brain/cerebral region. In some embodiments, it may comprise one or more LEDs manufactured into a single device, or in other embodiments, multiple LEDs may be used at different physical locations. Naturally, while a broad IR range of 600 nm to 1000 nm is presented here as an example, it will be appreciated upon further reading that different shorter or longer ranges can be considered without departing from the general scope and nature of the present disclosure. Similarly, a collection of wavelengths within the broad IR range of 600 nm to 1000 nm may be selected to represent the broad IR range. It will also be appreciated that different light sources and/or combinations of light sources 106 may be considered to provide such range, to accommodate different probing spectrum intensity or continuity profiles, or the like, without departing from the general scope and nature of the present disclosure. Furthermore, while focus is made on a broad-spectrum IR light source, other complementary spectral regions may also be considered where absorption, transmission and/or reflectance spectra can provide complementary information or characteristics on blood-oxygen, blood hydration or other blood-constituent elements of interest.

In this embodiment, probe 102 further comprises at least one high-resolution miniature spectrometer or sensor 108 to record one or more high-resolution absorption or transmission spectra of the transmitted or reflected light from light source 106. Miniature spectrometer 108 may take different forms and/or have different specifications. In general, spectrometer 108 should have a high spectral resolution sufficient to confidently reproduce a representative spectral signature received by probe 102 over the broad-spectrum IR or near-IR range of interest. In some embodiments, spectrometer 108 may be based on a diffraction grating design, a multi-layer filter design, a combination thereof or another design entirely. For example, and without limitation, spectrometer 108 may be operable to acquire spectral data with a 5 nm resolution over the whole range between 600 nm to 1000 nm (e.g. 10, 40 or even 80 distinct wavelengths/spectral regions). The skilled technician will understand that different numbers of wavelengths with different resolutions may be considered. In general, the acquired spectral data should have a resolution that allows to differentiate between different peaks or troughs (dips) of interests, with sufficient details so as to allow for comparative analysis of such acquired spectra with designated representative spectra or spectral variations therein, and/or with previously or continuously acquired spectra as a user's condition and/or environment changes. Namely, as will be detailed below, acquired spectra may be used for comparative analysis as a single diagnostic or screening tool against preset or designated standard spectra representative of healthy, low risk or high risk conditions, illnesses, and/or environmental scenarios, or again as continuous or regular monitoring means whereby observed spectral profile variations in different spectral regions or combinations of such regions can be quantitatively or qualitatively mapped to corresponding conditions or risk factors. In the case of the latter, wherein acquired spectra may be used for continuous monitoring, spectral profile variations may be observable in real-time wherein skilled technicians may infer associated conditions or risks without the need for specific mapping.

With continued reference to FIG. 1, different configurations of light source 106 and spectrometer 108 may be considered for probe 102. In some embodiments, a single light source 106 and spectrometer 108 may be used. For example, a single broad IR spectrum LED and a single sensor may be used, with a pre-defined distance therebetween. In some embodiments, sensor 108 and the single LED of light source 106 may be placed opposite each other (e.g. with the tissue of interest in-between) so as to measure the transmission (or absorption) spectra. In other embodiments, a linear configuration may be used where the LED of light source 106 and sensor 108 are placed next to each other (as shown in FIG. 1), pointing in the same direction, in order to measure the light scattered back from the tissue volume they are placed on.

In yet another embodiment, one sensor/spectrometer 108 may be placed linearly alongside a light source 106 comprising multiple LEDs (reflection-type design). In this configuration it may be possible to have different pre-defined distances between each LED and sensor 108. The difference in distances may thus allow for spatially-resolved data to be acquired.

In yet another embodiment, probe 102 may consist of a light source 106 comprising a single LED, but with sensor 108 comprising several individual sensors instead of a single device, e.g. several sensors laid out in a linear spatially-resolved reflection-type configuration. This layout thus also allows spatially-resolved spectrometric data with different pre-defined distances between the single LED and each sensor.

Going back to FIG. 1, in the illustrated exemplary embodiment, probe 102 is shown as comprising two detectors 108 with a single LED infrared light source 106, placed on or affixed to a mounting platform or casing 110 that holds them in place on the forehead in proximity to the frontal cortex when the user is wearing headband 104. While in this exemplary embodiment, a headband is used, the skilled technician will understand that other designs may be used, for example that include smaller patches that can be affixed with medical adhesive or through suction cups. Moreover, other body areas may be targeted with different means of affixing probe 102 thereto, without limitation. For example, a wrist of a user may be targeted, with the mounting platform or casing 110 being disposed in a wristband 104. In another example, an extremity of a user may be targeted, with the mounting platform or casing 110 being disposed in a band 104 adapted to fit to an extremity.

In addition to probe 102, platform or casing 110 of FIG. 1 further contains the electronics and energy source necessary to power and control probe 102 and communicate to an external computer. For example, this may include a digital data processor 112 communicatively connected to an internal memory 114, a power source 116 and a communication device 118.

Digital data processor 112 may be any type of digital data processor known in the art, or otherwise developed and capable of meeting the processing needs of system 100. This may include low-powered microcontrollers, embedded processors or the like. Generally, digital data processor 112 is communicatively linked to probe 102 so as to at least control its operation and sometimes additionally process, at least in part, the acquired data. Digital data processor 112 is also communicatively linked to internal memory 114 which may contain for example instructions for use thereby. Internal memory 114 can be any form of electronic storage known in the art (or otherwise developed for memory storage), or a combination thereof, including read-only memory, random-access memory, or flash memory, to name a few examples. Power source 116 may comprise one or more rechargeable or non-rechargeable batteries. Communication device 118 may be any device operable to transmit data to another electronic device. This may include a network adapter for transmitting data over a wired (i.e. ethernet) or wireless connection (i.e. Bluetooth or Wireless Fidelity (Wi-Fi) protocols). It may also include radio frequency (RF) emitters/transmitters, for example a wireless universal asynchronous receiver-transmitter (UART) RF module or similar. In the illustrated embodiment of FIG. 1, communication device 118 is shown transmitting data via a wireless signal 120 to a remote processing device 122. The skilled technician will understand that other electronic components may also be integrated on probe 102 as required. These may include, for example, DC/DC converters, or any electronic component required to assist, improve or optimize the functioning of the components already discussed above, without limitation.

In some embodiments, probe 102 and its associated electronic components may be operable to function in an offline mode in which case the data is stored on board in internal memory 114 for future download once the wireless link 120 is made available. The device 102 may also function in an online mode when the wireless connection 120 to remote device 122 is available and can allow real-time download of the data acquired for monitoring and processing purposes.

In some embodiments, remote device 122 may be any type of a computer with a digital display screen, tablet, smartwatch, smartphone or like general computing device. It generally comprises its own communication device 124 configured so as to communicate with communication device 108 of the probe 102, an internal memory 126, a digital data processor 128, some type of display 130 and one or more input devices 132 (i.e. keyboard, mouse, touch screen, etc.). In some embodiments, remote device 122 may be operable to receive spectral data acquired by probe 102 and to process it.

In some embodiments, as remote device 122 may not have the constraint otherwise imposed on a wearable probe such as that provided by headband 104, digital data processor 128 may be more powerful than digital data processor 112 on headband 104, and may thus be relied on to provide more demanding tasks such as data analysis or the like. In other embodiments, if remote device 122 is also lightweight (e.g. smartwatch, etc.), processing may be offloaded, at least in part, to a remote server or similar (not shown) to which remote device 122 is or can be remotely connected.

Figure 2:
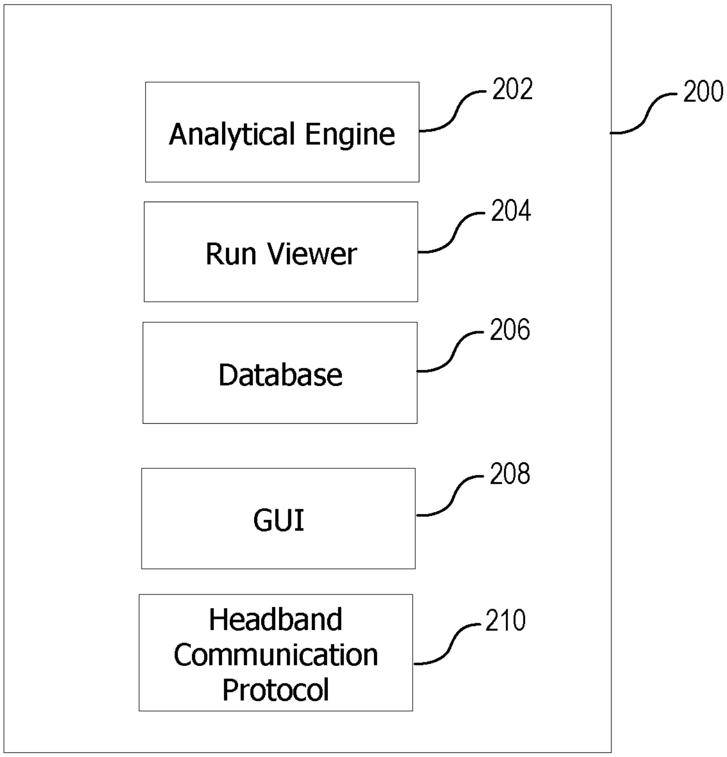
FIG. 2 is a schematic diagram of an exemplary software processing system, in accordance with one embodiment.

With reference to FIG. 2, and in accordance with different embodiments, a software processing system or engine for processing spectral data, generally referred to using the numeral 200, is discussed. In this exemplary embodiment, processing system 200 may be executed on remote device 122, which is in direct communication with the electronics of probe 102 on headband 104 as mentioned above. More generally, in some embodiments, processing system 200 may be in the form of a software interface or application interface running or being executed on a computer with a digital display screen, tablet, smartphone application or like general computing device, or again a dedicated device having a graphical or like general computing device.

In some embodiments, processing system 200 may comprise one or more software modules or features, including for example an analytical engine 202, a run viewer 204, a database 206, a graphical user interface (GUI) 208 and/or a headband communication protocol interface 210.

In some embodiments, analytical engine module 202 comprises software configured or programmed to process spectral data acquired by probe 102. This may include fitting the spectral data with one or more spectral functions so as to determine the spectral contributions from one or more chromophores or molecules. It may also include using the identified spectral contributions from each chromophore (and thus a related chromophore concentration) to derive one or more related physiological or health-related parameters. These may include, without limitation, blood volume, blood flow rate, breathing rate, blood-oxygen transfer rates, oxygen transfer rate, heart rate, blood pressure, blood or tissue hydration levels, and/or any medical condition or ensuing medical condition related to a change thereof. In some cases, this may be done using pre-defined analytical models. In other cases, machine-learning or artificial intelligence (AI) algorithms may be used to derive correlations between these one or more physiological parameters and the spectral contributions. Moreover, by combining an analytical model with the high-resolution spectral data acquired by probe 102, absolute measurements are possible, in contrast with known methods which rely on relative measurements. Therefore, in obtaining measurements (absolute or relative to a baseline, as the case may be) which may be displayed, for example, as percentage values or otherwise graphically, healthcare practitioners may be able to readily observe fluctuations in measurements and based on their own knowledge of a patient, medical conditions and the current scenario, in turn reach their own conclusions as to the physiological parameters.

In some embodiments, run viewer module 204 is a program operable to monitor spectral data acquired via probe 102, in some cases in real-time. This may include generating plots or graphical representations of the spectral data. As mentioned above, graphical representations of the spectral data may be particularly useful in visualizing real-time measurement data obtained. In some embodiments, run viewer module 204 may further be used to remotely program or configure probe 102 or any parameter related to the spectral acquisition process (i.e. acquisition frequency, brightness of light source 106, etc.).

In some embodiments, database module 206 may include a database software, or a database-interfacing program operable to interface with a remote server-based database. It may be used to store spectral data acquired via probe 102 but also any processing done thereto via analytical engine 202. In some embodiments, previous measurements may be stored in database module 206 so as to construct a baseline for one or more physiological or health-related parameters. Such baseline may be, for example, patient specific based on previous measurements for a specific patient or otherwise a trend baseline.

In some embodiments, processing system 200 may include a headband communication protocol interface module 210. This may include any software used to configure or control data transmission between probe 102 and remote device 122 (or to any other computing device), so as to, for example, configure either one of communication devices 118 or 124. In some embodiments, this may also include configuring how other parameters related to the functioning of any components located on headband 104 may also be transmitted. For example, this may include the remaining charge of power source 116 or any error messages related to malfunctioning hardware components.

In some embodiments, processing system 200 may further comprise a GUI 208, displayed for example via display 130, and which may be used to interact with any one of modules 202 to 206 or 210 via a mouse or touchscreen. In some embodiments, multiple modules may be interacted with simultaneously via GUI 208.

In some embodiments, the software processing system or engine 200 for processing spectral data may be communicatively connected to a plurality of probes 102 attachable to a user body region at spaced apart positions. Such system 200 may be useful in an acute medical setting, for example, where a plurality of probes 102 can be attached at functional positions to work cooperatively to obtain transmission data for the user body region. Otherwise, the plurality of probes may be pre-arranged at functional positions in a wearable device, such as a cap, to obtain transmission readings in parallel. In such embodiments, system 200 may be executed on device which is in direct communication with the electronics of the plurality of probes 102, either wirelessly (system 200 being in the form of a software or application interface running or executed on a tablet or smartphone, for example) or via a wired connection (typically possible in a medical facility, system 200 being in the form of a software or application interface running or executed on a computer with a digital display screen, for example). In these embodiments, the analytical engine module 202 may comprise software configured or programmed to process spectral data acquired by the plurality of probes 102 in parallel or cooperatively, to more accurately represent regional concentrations of the chromophores or molecules so as to derive one or more related physiological or health-related parameters. It is to be further appreciated that the plurality of probes 102 may be attached to different user body regions, such as at the head and at the wrist, to obtain comparable data under the same conditions at different user body regions.

Figure 3:
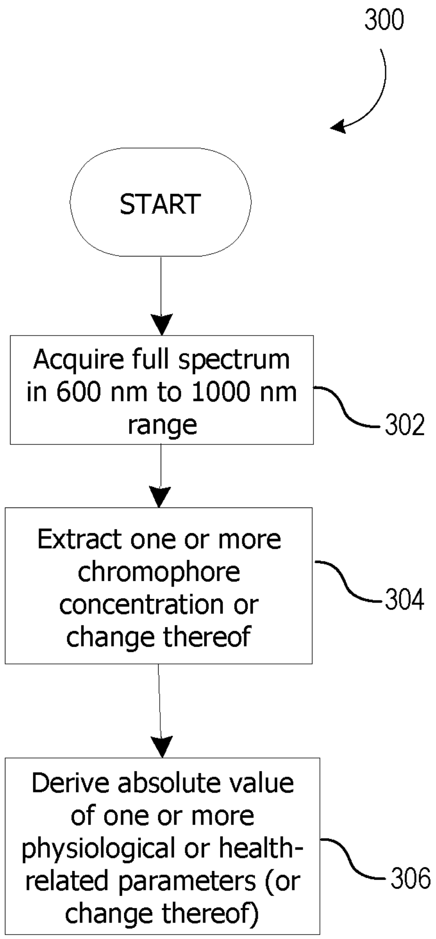
FIG. 3 is a process flow diagram illustrating a monitoring method for assessing certain physiological parameters using the system of FIG. 1, in accordance with some embodiments.

With reference to FIG. 3, and in accordance with one embodiment, a process for monitoring for one or more health-related parameters with system 100, generally referred to using the numeral 300, will now be described.

Initially, at step 302, a full or broad-spectrum profile (as a spectral signal or data, typically raw data) of a user or patient is acquired via probe 102. As mentioned above, the exemplary system 100 is designed so as to acquire a full spectrum between 600 nm and 1000 nm. Different resolutions may be used, for example and without limitation, a resolution of 5 nm from 600 nm to 1000 nm, or 81 wavelengths in total. In other embodiments, where a collection of wavelengths are utilized by system 100, such wavelengths may be selectively targeted based on known health-related parameters associated therewith and obtained with similar resolution of 5 nm per wavelength.

At step 304, the acquired spectral signal or data is analyzed or processed. In some embodiments, it may be preferable to directly send or transmit the acquired raw spectral data to remote device 122 for analysis (for example, to minimize the power requirements of wearable digital data processor 112). In other embodiments, the analysis, processing or pre-processing (i.e. averaging of multiple acquisitions or other) of the acquired spectra may be done, at least in part, via digital data processor 112 located on headband 104 before being transmitted.

As mentioned above, the high spectral resolution provided by system 100 provides a higher discrimination ability between various chromophores being monitored. These may include, without limitation, extracting concentrations for chromophores like carbon monoxide, cytochrome oxidase, oxyhemoglobin, deoxyhemoglobin, myoglobin or other hemoglobin types, melanin, etc. Blood volume changes can also be monitored, for example, where monitored concentrations remain relatively constant but a greater or lesser volume of probed chromophores (i.e. molecules) travel across the sensor's field of view over time. Chromophores (e.g. molecules) monitored may further relate to hydration levels, such water molecules or other related blood-borne chromophores reflecting hydration of a patient.

Furthermore, the high spectral resolution provided by system 100 provides a higher discrimination ability between changes in concentrations of such chromophores over time. Such concentration changes may be indicated based on, for example, absolute values acquired and not dependent on trend data.

The high resolution and the large range of the acquired spectrum allows, for example, spectral unmixing analysis, wherein the spectral signature can be broken down into its constituent spectral components and the relative proportion of each of these component spectra can be deduced. Typically, the spectral signature (or spectral profile) can be deconstructed into constituent spectral components or contributors via spectral deconvolution to identify for example overlapping spectral contributions in the spectral signature. This has the unique capability of being able to extract known absorption spectra from the at-sensor spectra and find "residual" signatures with spectra of unknown origin. Conversely, a spectral signature can be extracted based only on its unique feature distribution over the entire IR range. This allows better estimates of the material causing that signature. It also allows extraction of spectra with very broad features more accurately, which is not readily available using only a few token wavelengths in a conventional oximeter, since these broad spectra features are more affected by confounding factors. Thus, each spectral component or combination of spectral components can be resolved or identified (based on deconvolution or otherwise). In combination with an analytical model, this allows the calculation of absolute values. This is in contrast with current cerebral oximetry techniques which rely on the calculation of indices (regional saturation, etc.) based on ratios and these can only be relative to baseline measurements. This means that values from one patient to another may vary significantly and comparisons are therefore not easily done.

Different functions or functional forms may be used or fitted to the spectral data to extract distinct chromophore signatures therein. This may include different multivariate analysis methods known in the art for addressing the presence of two or more chromophore components having overlapping spectral features.

Moreover, while conventional cerebral oximeters tend to average readings or measurements over a period of several seconds to be able to output a steady reading, in contrast, system 100 may be operable, in some embodiments, to deconvolve the physiological parameters for each spectral reading acquired at a high frequency in order to remove any confounding effect and thus be able to render a high-frequency reading of all parameters, which avoids the need to overly average readings to remove those confounding effects. Similarly, while the averaging of conventional cerebral oximeters leads to updated average-based readings every few seconds, in contrast, system 100 may be operable, in some embodiments, to deconvolve the physiological parameters for each spectral reading acquired at a high frequency to provide real-time or near-to-real-time readings (which may be absolute readings in some embodiments), which allows real-time or near-to-real-time responses to the readings obtained. This may be particularly useful in life-threatening scenarios, as described further below. It is to be appreciated that, the frequency of deconvolution will depend on the physiological parameter (i.e. chromophores) or condition to be identified. Generally, the frequency should be at least 2 or 3 times that of the (known or expected) variation of the parameter of interest. For example, if system 100 is configured to monitor heart rate, and a pulse is to be deconvolved, system 100 will be operable to deconvolve the spectral readings at frequencies at least 2 or 3 times that of 60 to 200 beats per minute. Other frequencies for other parameters will be readily understood by those skilled in the art and are intended to fall well within the scope of the present disclosure.

The nature of spectroximetry, or hyperspectral oximetry, as in the case of system 100, allows measurement of absolute transmission of energy. Therefore, intra-patient and/or inter-patient measurements can be readily taken, for example, without significant pre-calibration efforts or techniques. This may be useful, for example, to compensate for known drawbacks of existing oximeters, such the different parameters that affect the accuracy of pulse oximeter readings, such as skin pigmentation, poor circulation, skin thickness, skin temperature, current tobacco use, and use of fingernail polish.

Once one or more chromophore absorption levels have been extracted from the spectral data, in step 306, these may be correlated with one or more physiological or health-related parameters, or with a change thereof. In some embodiments, the higher level of spectral information acquired by system 100 may allow to derive correlations with known clinical data using one or more optimization algorithms, for example using AI models or similar (including neural network models or deep-learning models).

Moreover, since the acquired spectral data covers a large range of wavelengths, this allows not only to compare spectra between users or patients, but it also allows customization of the diagnostic value or device response to the target individual.

These one or more physiological or health-related parameters may include, without limitation, blood pressure, blood or tissue oxygenation, pulse, blood flow rate, blood loss or hemorrhaging, cognitive assessments, lung efficiency, oxygen transport rate, rate of $O_2$ consumption by the brain or other physiological system being probed, stress detection, blackout warnings, CPR monitoring, sleep apnea (or other sleep disorder) monitoring, hydration or dehydration monitoring, assessment of vital signs, detection of strokes, etc. Some of these will be discussed further below. Moreover, since system 100 is operable to acquire high-frequency spectral data which contains the presence of multiple chromophore signatures simultaneously, it may thus allow for a synchronization of correlations between the one or more physiological or health-related parameters derived therefrom.

In some embodiments, the absolute nature of the absorption spectra acquired by probe 102 may allow to detect blood loss, or hemorrhaging. For example, while the oxygen saturation (SpO2) parameter measured using traditional oximetry techniques only considers the fraction of the hemoglobin molecules in the oxygenated state (i.e. oxyhemoglobin) and not the total hemoglobin content, it cannot provide an absolute reference value from one individual to another. Indeed, it can only provide a measure of the portion of hemoglobin molecules which are/are not oxygenated (i.e. oxyhemoglobin or deoxyhemoglobin). In contrast, system 100 is operable to provide a more complete spectrum (or a more complete spectral profile based on selected wavelengths, as the case may be) and may thus be able to assess the level of hemoglobin concentration from the total absorption of light. Otherwise, a total oxygen concentration may be assessed from the total absorption of light. In the exemplary case of blood loss, system 100 may detect the total concentration of hemoglobin going down, even when the oxygen saturation remains at 100%. In other embodiments, the absolute nature of system 100 may facilitate monitoring of health-related parameters (oxygenation levels or otherwise) even when oxygen saturation (SpO2) level is below 80%.

In some embodiments, system 100 may provide diagnostic evaluation via the use of bolus type tests in which an "indicator" (e.g. naturally occurring or foreign tracer molecule or similar) is introduced in the blood and its effects are measured, in some embodiments in real-time. For example, a patient may receive a shot of high concentration $O_2$ (e.g. 100% $O_2$), which may be detected via a spike in measured venous oxyhemoglobin, which may be detected in the head, neck, wrist and/or other monitored region. If the initial amount of $O_2$ introduced is known, system 100 may derive therefrom a concentration of new oxyhemoglobin, which, combined with a measurement of the change in absorption of light in the head (or other region), may be used to derive a venous blood optical "thickness" value. The same process may also be done when monitoring arterial oxyhemoglobin and consequently, a corresponding proportion of arterial to venous content in the head can be derived. For instance, if the amount of new arterial oxyhemoglobin resulting from the "shot" of $O_2$ is estimated, then changes measured in the oxyhemoglobin absorption can be fitted to a venous volume required to manifest the total spectral absorption observed, thereby providing an indication as to arterial to venous proportions. Other tests may include, but are not limited to, pulmonary efficiency, in that knowing an increase in $O_2$ molecules introduced, one can measure what amount reaching the blood (e.g. via spectral absorption) and qualify or quantify a proportion of the $O_2$ being absorbed into the blood and/or a speed or efficiency at which it is so absorbed. These and other similar tests may be done by system 100 in real-time for each individual. Furthermore, where system 100 includes a plurality of probes 102, the probes may be attachable at different user body regions (e.g. the head and the wrist) of the individual to obtain comparative data of the effect of the $O_2$ bolus at different regions.

In some embodiments, the same "bolus" type test may also/be used to provide the time of travel between the lungs (where $O_2$ is exchanged) and one or more points of interest on the body (e.g. head, extremities such as arms, fingers, feet or legs as a function of blood pressure). This type of measurement may be used to derive a blood flow rate value, for example, or otherwise an oxygen transport rate. In particular, such tests may relate to the time delay between oxygen introduction and changes in oxygen concentration at the point of interest, which changes are observable with system 100 with a resolution allowing individual bolus detection, as described further below.

Similarly, since blood flow rate is dependent on blood pressure, similar correlations between flow rates and blood pressure may be derived. Currently, correlations derived using a conventional pulse-oximetry signal and blood pressure are statistically-based and use databases of previously measured signals to optimize an algorithm (such as AI). In contrast, the full or broad-spectrum approach provided by system 100 (or selected wavelengths representative of a broad-spectrum) is more versatile, as it is based on direct correlations between different physiological parameters.

In some embodiments, detected changes in oxyhemoglobin and deoxyhemoglobin may be combined with the $O_2$ content being inhaled (e.g. the % $O_2$ being inhaled), to derive a level of dissolved oxygen in the blood. It is to be appreciated that conventional oximeters, which rely on two wavelength measurements specifically directed to oxyhemoglobin and deoxyhemoglobin respectively, may lack capabilities to obtain dissolved blood oxygen levels. Nonetheless, dissolved oxygen levels are in some instances important health indicators as dissolved oxygen (located in plasma and red blood cell water) amounts to 2% of total oxygen in blood on average.

In some embodiments, system 100 may be configured to detect an increase in the optical density related to oxyhemoglobin in the venous blood, and may use the concentration of $O_2$ being inhaled (e.g. the % $O_2$ being inhaled), to derive a corresponding hemoglobin concentration. This may also be done when measuring a decrease in optical density of oxyhemoglobin with a decreasing concentration of $O_2$ being inhaled.

In some embodiments, system 100 may be used to monitor $O_2$ delivery. For example, in some clinical settings, it may be desirable to administer $O_2$ to a patient to increase the partial pressure of $O_2$ in the patient's lungs and the blood. However, elevated concentrations of $O_2$ in the blood for prolonged time are known to have detrimental effects. Conventional pulse oximeters are not able to show if the patient is in a hyperoxic state (or above partial pressure of 0.21 ATA). In contrast, full or broad-spectrum oximetry as provided by system 100 may be operable to track elevated $O_2$ states. System 100 may also be operable to detect dropping $O_2$ levels before a hypoxic state is even reached (including when individual is in a hyperoxic state, thus predicting a hypoxic state prior to reaching it), in contrast to a pulse oximeter that would typically only be able to detect the hypoxic state once reached.

In some embodiments, system 100 may be used in hyperbaric medicine. For example, in some embodiments, system 100 may be configured to track hyperoxic states well above a $O_2$ partial pressure of 0.21 ATA, thus allowing the monitoring of how close the patient is to hazardous levels of oxygen toxicity.

In some embodiments, system 100 may be used for cognitive assessment during sports or in extreme environments. For example, system 100 may be configured to provide assessment of oxygenation levels during exercise. It is well known that conventional oximetry does not see or detect increases in blood oxygenation beyond SpO2 of 100%, which is very close to the value anyone has normally at rest. In contrast, system 100 may be operable to observe or detect increases in the level of oxyhemoglobin reaching the organ of interest (e.g. brain) in a specified unit of time during exercise. For instance, this may be used to indicate an increase in blood flow, and thus of oxyhemoglobin, to the organ under observation, which may translate to a greater delivery of $O_2$ to that organ. Thus, in some embodiments, system 100 may be used to monitor or assess the level of increased oxygenation from one activity to another, which may be used to create a baseline by finding normal increases in oxygen delivery to the brain (or other organs) using a sample population. Thus, measurements from an individual may be compared to this baseline and this used to assess performance, impairments, etc.

In some embodiments, system 100 may be configured to monitor the rate of $O_2$ consumption (or metabolism) in the brain or other organ or region of interest. For example, with normal air, arterial blood is almost 100% saturated. If 100% $O_2$ is inhaled, the venous deoxyhemoglobin in an organ will decrease by an amount proportional to the amount of $O_2$ not metabolized by the tissue under study. Thus, by knowing the input quantity or amount of air (specifically $O_2$ content) and knowing what is left over from the dissolved $O_2$ that went back into the venous hemoglobin (thus raising its oxyhemoglobin content), system 100 may be configured to derive the portion of $O_2$ taken up by the organ of interest (i.e. metabolized). In some embodiments, this may be done on a population sample which may then be used as a reference or baseline for diagnostics of other individuals.

In some embodiments, system 100 may be operable to derive a lung efficiency value or similar. Such lung efficiency value may, for example, be valuable in conjunction with other more generic pulmonary function tests (PFTs).

By introducing a known increase in $O_2$ content being inhaled and measuring the effective change in oxyhemoglobin and deoxyhemoglobin, and if applicable, knowing the metabolized amount in the tissue under investigation, system 100 may derive therefrom a measure of efficiency of $O_2$ transfer occurring at the pulmonary level. Conversely, $O_2$ intake may be reduced and system 100 used to monitor the corresponding decrease of oxyhemoglobin optical density (and/or increase in deoxyhemoglobin) in the arteries.

In some embodiments, system 100 may be operable to derive a concentration of $O_2$ inhaled. This may be done as described above for assessing lung efficiency, but here assuming a fixed level of lung efficiency to derive the concentration being inhaled. In some embodiments, system 100 may thus be combined or used in conjunction with a rebreather diving apparatus or similar.

In some embodiments, system 100 may be used for stress detection and assessment. For example, stress in a user or patient impacts physiological parameters such as pulse, respiration, and blood flow rate. All these parameters may be correlated to the spectra recorded via system 100. An assessment on the stress level can be made using a combination of known states for each parameter, as well as known changes to these parameters (i.e. sudden increase in heart rate and breathing).

In some embodiments, system 100 may be configured to alert for imminent blackout in an individual or user. The onset of blackout in a user may be predicted based on the oxygenation state of the person. For example, for military pilots, a drop of blood flow to the brain, or a drop of oxygenation levels, as monitored by system 100, may be used to mitigate risk of blackouts.

In some embodiments, system 100 may be used to monitor cardiopulmonary resuscitation (CPR) maneuvers or the like. Currently, CPR is performed using set recommended protocols and procedures for the frequency of chest compressions and mouth-to-mouth assisted breathing (or rescue breathing). These protocols are established based on experience of healthcare professionals. Means for an assessment of the performance of CPR given to a patient in real-time while CPR is administered can significantly improve patient outcome. The protocol could be adapted to the patient's needs given the specific scenario and the specific patient response. Some devices in the art have attempted to inform CPR protocols by providing output reflecting an overall trend of increased or decreased oxygen. However, one of the problems with traditional cerebral oximetry is the lack of common baseline from one patient to another. It is also not clear what values given by one instrument should be used as target since (1) the index is relative, (2) indices are not calculated the same way, (3) the same index can vary from one device to the next due to design factors, (4) lack of clinical studies across all devices, (5) variability in readings from one patient to another using the same device given skin type, ethnic background, etc. Another significant disadvantage of traditional cerebral oximetry is the fact that the index typically is calculated using an integration time significantly longer than a normal heartbeat. Sensitivity to minute changes in hemoglobin is therefore compromised. Finally, conventional pulse oximetry will not work when the patient has a weak or no pulse. The system 100 may provide, in some embodiments, a system suitable for informing CPR administration in real-time without the limitations of existing devices, as described further below.

Full spectrum oximetry as provided by system 100 may allow for the instantaneous assessment of vital signs (or at least, in near real-time so as to appear to be instantaneous). For example, by deconvolving spectral signatures, individual contribution of each type of chromophore (or molecule) may be measured. High-frequency measurements can allow observation of variations in blood flow (or other relevant health parameter) that could be indicative of chest compressions. This approach can also define a target "absolute index" of absorption in the brain caused by oxyhemoglobin, blood flow, and other useful parameters. This index can be then be used for all individuals.

In some embodiments, system 100 may be configured to detect strokes resulting from the blockage of blood flow to the brain. As discussed above, reduction of blood flow may be derived by system 100 via a significant reduction in absorption of key spectral responses (herein being spectral indicators).

Conventional oximetry devices and systems typically do not directly reflect hydrations levels. Water molecules, which are the main constituent of living tissue, also render transmission spectra and most features in the near-IR spectral region beyond 950 nm are the result of absorption bands of water. In some embodiments, system 100 may be used to monitor hydration (or dehydration) levels at the user body region, particularly in the range of 600 nm to 1000 nm and based on water molecules in tissue. In these embodiments, the spectrometer (or processor, as the case may be) may be operable to resolve or isolate from the optical signal a distinguishable spectral response in the broad-range illumination corresponding to hydration. In one embodiment, the spectrometer (or processor, as the case may be) may be operable to resolve or isolate from the optical signal a distinguishable spectral response in the 950 nm absorption line reflective of hydration in tissue. Although the absorption spectra for water is fairly broad, it is known that the 950 nm absorption line is predominantly affected by water levels in the blood, making this feature particularly useful in monitoring hydration levels. This hydration monitoring application of system 100 may be available in addition to some of the other applications of system 100 described herein, particularly including the various oxygen monitoring applications. Hydration monitoring applications of system 100 may typically relate to skin hydration, although deeper tissue hydration monitoring may also be possible.

It is to be appreciated, of course, that any two or more of the applications of system 100 may be simultaneously monitored to provide an indication of an overall health of the user. In the same vein, any two or more distinct spectral responses may be resolved or isolated in parallel for the same purpose.

Figure 4:
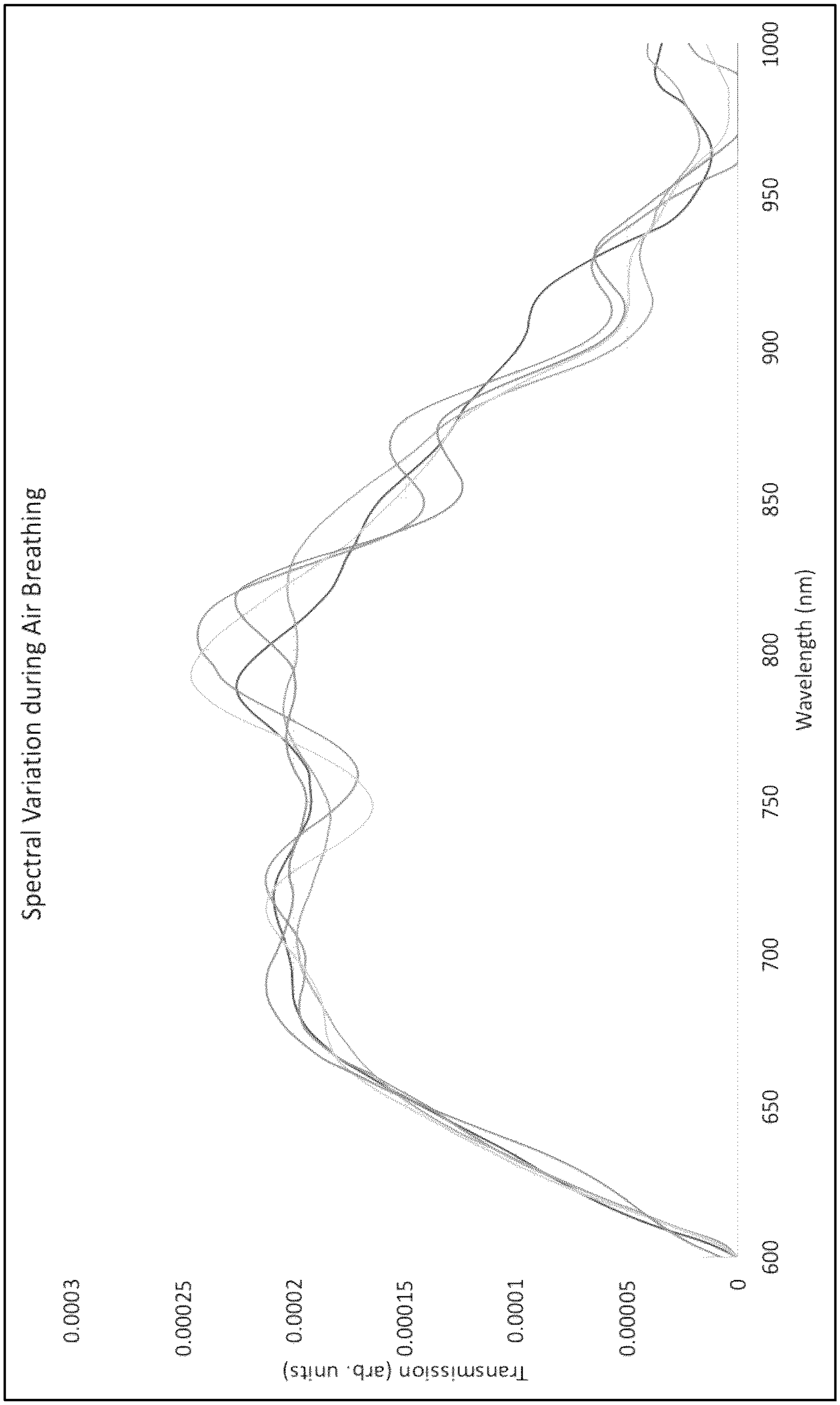
FIG. 4 is an exemplary plot of a spectral variation measured in (a cerebral region of) a user breathing normal air while sitting in a chair, in accordance with one embodiment.
Figure 5:
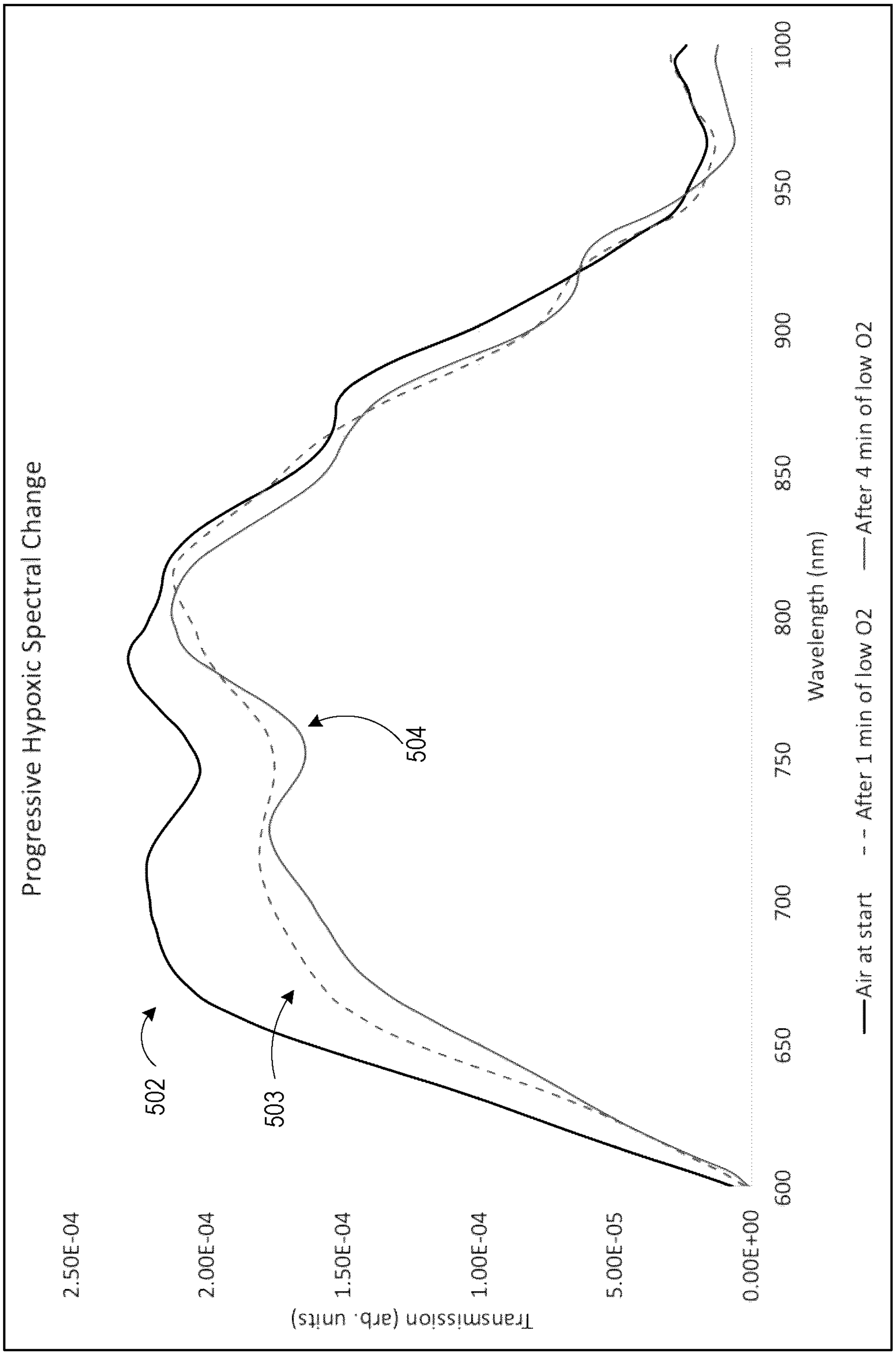
FIG. 5 is an exemplary plot of an average change in recorded spectra (in a cerebral region) when switching from normal air (21% $O_2$) to a hypoxic gas containing 5% $O_2$, in accordance with one embodiment.
Figure 6:
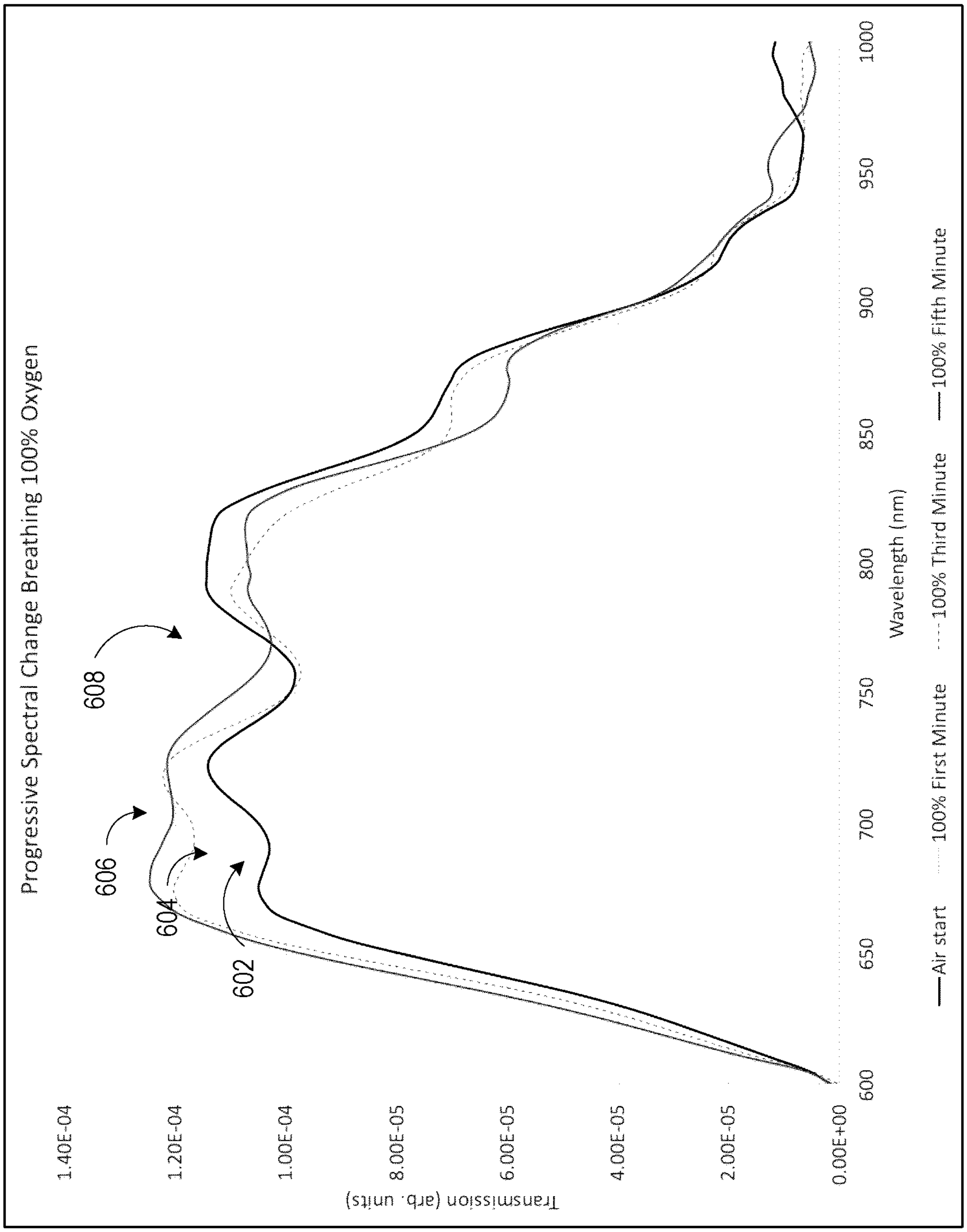
FIG. 6 is an exemplary plot of an average change in recorded spectra (in a cerebral region) when switching from normal air (21% $O_2$) to breathing pure oxygen (100% $O_2$), in accordance with one embodiment.

With reference to FIGS. 4 to 6, and in accordance with one exemplary embodiment, an exemplary set of measurements acquired using an exemplary embodiment of system 100 will be discussed.

FIG. 4 shows an exemplary plot of multiple spectral transmission curves acquired at the cerebral level for a user wearing system 100 and breathing normal air while being in a seated position. The plot shows randomly acquired spectra over a two-minute period. The time sampling of repeated measurements (i.e. different curves) shows variations that are due to the inherent physiological changes caused by varying blood flow (heart beats, blood pressure, etc.), breathing rate, and other such normal body functions. Spectra taken at various times therefore will show variations in the acquired spectra due to these inherent physiological changes. This allows system 100 to derive values for physiological parameters such as pulse, blood flow, head orientation, blood volume, blood pressure, blood hydration, etc., which are appreciated to be health-related, with adequate modeling, since the spectral differences can be used to derive the physiological parameters that affect these readings such as pulse, blood volume, blood volume, blood pressure, blood hydration etc. In some embodiments, the transmission curve of normal air at 21% $O_2$ (FIG. 4) can represent a baseline to which changes arising from different $O_2$ concentration present can be interpreted.

With reference to FIG. 5, a plot showing an average change of spectral readings when switching from normal air breathing (with 21% $O_2$), as seen in the previous FIG. 4, to breathing a hypoxic gas that contains 5% $O_2$ will now be discussed. Breathing a hypoxic gas results in a significant (but proportionate) lowering of the level of oxygen reaching the blood and tissues (due to less oxygen being exchanged at the alveoli). The plot of FIG. 5 shows the progressive change in spectral readings with line 502 representing an average of multiple spectra taken during one-minute breathing air in a sitting position, as in the previous plot of FIG. 4. Meanwhile, line 503 shows the average of multiple spectra taken after a minute of breathing the hypoxic mix. Finally, line 504 is the average of multiple spectra taken after breathing 4 minutes of the hypoxic mix. In this case, there is a clear decrease in the transmission in the 700 nm area which is consistent with an increase in absorption due to elevated deoxyhemoglobin levels.

Similarly, FIG. 6 is a plot showing various acquired spectra when the user switches from breathing normal air (21% $O_2$) to breathing pure oxygen (100% $O_2$). Line 602 shows the average of multiple spectra taken during the first minute of breathing normal air. Lines 604 and 606 are the average of multiple spectra acquired during the first and third minutes, respectively. Line 608 is the average of multiple spectra acquired during the fifth minute of breathing pure oxygen. While conventional pulse oximeters, as well as cerebral oximeters (regional saturation) would not show significant change in these conditions, the full-spectrometric signals acquired via system 100 clearly show the progressive change related to the changing breathing conditions. Embodiments of system 100 discussed below provide comparative data supporting this.

In accordance with another aspect of the present disclosure, there is provided an oximetry system for temporally monitoring oxygen levels at a user body region in real time. The features of this system largely reflect the system described with reference to FIG. 1, thus like reference numerals are utilised where applicable below.

Oximetry system 100 for temporally monitoring oxygen levels at a user body region in real time comprises an oximetry probe 102 attachable to the user body region. The oximetry probe 102 comprises a light source 106 providing illumination to the user body region within a designated spectral region to probe various blood-borne chromophores exhibiting respective spectral responses within the designated spectral region, and a spectrometer 108 operable to acquire an optical signal from the user body region resulting from the illumination so to digitally capture a response including the respective spectral responses. Oximetry system 100 further comprises a digital data processor 112 operatively connected to the oximetry probe 102, and operable to process the response in real time to automatically identify temporal variations therein representative of oxygen delivery variations at the user body region, wherein the temporal variations are identifiable with a resolution allowing individual physiological event identification in real time.

In this example, light source 106 comprises a broad-spectrum light source which provides broad-spectrum illumination. More specifically, in this embodiment, the broad-spectrum light source 106 comprises a full spectrum infrared (IR) light source. Accordingly, oximetry probe 102 in this embodiment is in the form of a broad-spectrum oximetry probe. In other embodiments, conceivably where a broad-spectrum light source may be cost prohibitive, the light source may comprise one or more light sources capable of emitting infrared light necessary to probe the various blood-borne chromophores associated with oxygen.

In this embodiment, the designated spectral region comprises a range of about 600 nm to about 1000 nm. As described above but repeated here for clarity, the IR transmission spectra of tissue within this range reveal several "features of interest", particularly insofar as they relate to associated health indicators. Digital data processor 112 is specifically operable to isolate at least three distinct spectral regions from the broad-spectrum response, reflecting transmission from one or more blood-borne chromophores in the broad-spectrum response. Therefore, the spectral regions isolated typically correspond to regions which are known or otherwise suspected to reflect features of interest. Of course, depending on the application of system 100, and the health indicators to be monitored, certain features are of more interest than others. In this particular embodiment, digital data processor 112 is operable to isolate 10, 40, or 80 distinct spectral responses within the response.

As described above, conventional oximetry uses discreet wavelengths (typically only two, sometimes up to four or more) and therefore samples the IR transmission at specific points across the transmission range, depending on the features of interest to the user (typically only probing for oxyhemoglobin and deoxyhemoglobin). Conventional oximetry provides intensity measurements at those discrete wavelengths but cannot be used to deduce the spectral signature that gave the data, understanding that there are many transmission spectra that can lead to the same measured data. The fewer the wavelengths sampled, the greater the number of solutions to the possible spectra. Whilst this may render conventional oximetry based on four wavelengths better than two wavelengths, a large amount of data and potential transmission spectra still remains available.

On the other hand, system 100 as described herein (i.e. spectroximetry) aims to capture a unique solution to the IR transmission measurement, based on selectively targeting a broad range of known spectral responses (i.e. broad range spectroscopy). In this manner, all "features of interest" are measured and can be observed. In turn, this significant increase in information (based on the broad range probing) allows advanced spectral analysis techniques with a drastically greater level of discrimination possible (i.e. improved detectability), specifically of the elemental components that make up the observed spectra. This may be useful in identifying discrete physiological events associated with known chromophores or spectral responses.

In addition to allowing identification of the "features of interest", system 100 further allows any "spectral shifts" occurring in these features to be observed or identified. Such spectral shifts can be significant in interpreting the data obtained from the broad-spectrum response, particularly to derive a physiological assessment of a patient. One example of such spectral shift is the location of a local feature maxima which may change given a confounding factor. By only probing a few discrete wavelengths, as described above, conventional oximetry cannot detect these spectral shifts (particularly when the shift moves the local feature maxima outside the sampled range). Some embodiments of system 100, in contrast, enable spectral shifts to be observed in the output and thus accommodate confounding factors.

Put differently, system 100 provides more spectral data than the individual or discrete wavelengths considered in isolation, due to the collective or broad-range nature of spectroximetry or hyperspectral oximetry.

In this embodiment, the digital data processor 112 is specifically operable to output a time-variable integrated response amplitude, and thus the temporal variations in this embodiment comprise temporal variations in the time-variable integrated response amplitude. See, for example, FIGS. 7 to 10, which are discussed further below.

The digital data processor 112 is further operable, in this embodiment, to derive from the time-variable integrated response amplitude a temporal blood oxygen index. See, for example, FIGS. 11 and 12, which are obtained from FIGS. 7 and 8, and which are discussed further below. It is from this temporal blood oxygen index, in this embodiment, that the temporal variations in blood oxygen levels are determined by system 100, as described below, with resolution allowing individual physiological event identification.

In other embodiments, not shown, the digital data processor may be operable to isolate at least three distinct spectral responses (specifically, more than two) in different spectral regions of the response. In such embodiments, the digital data processor may be operable to isolate 10, 40, or 80 distinct spectral responses representative of one or more blood-borne chromophores of the response. In this context, isolating may involve, for example, identifying (by spectral decomposition, spectral unmixing or otherwise breaking down the response to identify the distinct spectral response) and quantifying transmission in each spectral wavelength region (or otherwise deducing relative portion of each component region). Spectral wavelength regions, in turn, may include the resolution acquired for a wavelength (i.e. for 650 nm with a resolution of approximately 5 nm, the wavelength region may comprise 645 nm to 656 nm). Furthermore, the digital data processor may be operable to extract a concentration of each of the various blood-borne chromophores from the respective spectral responses. From these concentrations, temporal variations may be determined by system 100. In some embodiments, these concentrations may be combined with one or both of the time-variable integrated broad-spectrum response amplitude and/or the temporal blood oxygen index to increase accuracy and/or resolution of temporal variation monitoring by system 100.

Returning to the present embodiment, the digital data processer 112 is further operable to store the response on a memory to configure a user-specific blood spectral index (otherwise referred to as a user-specific baseline). The response stored may be in the form of the raw data of the response, the time-variable integrated response amplitude, the temporal blood oxygen index, or any other representation of the response suitable for storage. The digital data processor 112 is further operable, in this embodiment, to compare the response with the user-specific blood spectral index. Thus, the user-specific blood spectral index forms a reference point (or baseline) against which future responses obtained by system 100 can be compared. Otherwise or in addition thereto, the digital data processor 112 may be operable to compare the response with a user-agnostic blood spectral index (or user-agnostic baseline). For example, the digital data processor 112 may be operable to feed a machine learning model with the response to train it, thereby providing a user-agnostic blood spectral index which can be utilised for such comparisons. In turn, training a machine learning model with the response may lead to a diagnostic tool capable of predicting a user outcome, for example with reference to successful and/or unsuccessful resuscitation of a user, or other possible user outcomes.

In other embodiments, the digital data processor 112 is operable to predict a user outcome based on the temporal variations and any one or both of the user-specific blood spectral index, or the user-agnostic blood spectral index. In such embodiments, the user-agnostic blood spectral index may include, for example, one or more risk thresholds for various user outcomes. The user outcome may be related, for example, to minor injury, serious injury (e.g. brain damage due to oxygen deprivation), survival (e.g. successful resuscitation) or death (e.g. unsuccessful resuscitation). Other possible thresholds and associated user outcomes (otherwise referred to as patient outcomes) may be conceived and are intended to fall well within the general scope and nature of the present disclosure.

The digital data processor 112 is further operable to determine an oxygen transport delay in this embodiment. The oxygen transport delay is calculated by the digital data processor 112 by calculating an elapsed time between receiving notification of one or more physiological events (discussed below) and identifying an associated temporal variation in the broad-spectrum response. The oxygen transport delay may refer to a delay between oxygen provided at the lungs and arrival thereof at the user body region. Other factors, such as expected oxygen consumption at the user body region, may also inform calculation of the oxygen transport delay. As skilled technicians will readily appreciate, the oxygen transport delay may be associated with, for example, user blood pressure, blood volume, user oxygen inhalation capacity and/or any other health conditions experienced by the user (or diagnostic evaluation of such health conditions).

In other embodiments, the digital data processor 112 may be further operable to extract a concentration of the one or more blood-borne chromophores from the respective spectral responses. System 100 combination with an analytical model, this allows the calculation of absolute values. Such concentration may provide to a user an indicator which is easily understandable, particularly in an emergency scenario. Such concentration may also be associated with a previous concentration, such that the digital data processor 112 may output an indicator reflecting, for example, increased concentration or decreased concentration.

The oxygen delivery variations at the user body region typically comprise any one of: an oxygen concentration increase, an oxygen concentration decrease, or a relatively unchanged oxygen concentration. As mentioned, in this embodiment, these oxygen delivery variations are temporally associated with one or more physiological events experienced by a user. Some physiological events may result in an oxygen concentration increase, which include: inhalation by a user; intubation of a user; mechanical administration of CPR to a user (whether administering a chest compression or a rescue breath); or the like. In some embodiments, events externally delivered and resulting in an oxygen concentration increase may be termed "oxygen boluses". Other physiological events may result in an oxygen concentration decrease, which include: an obstructed airway of a user; sleep apnea of a user (or other sleep disorders); cardiac arrest of a user; or the like. The temporal resolution of system 100 allows each individual physiological event to be identifiable in real time, through its associated temporal variation representative of the oxygen delivery variation. Thus, if the physiological event is a chest compression, the associated individual temporal variation in the response will be identified by system 100 as an oxygen concentration increase.

System 100 is, in this example, operable in the absence of a detectable pulse at the user body region. Therefore, system 100 can detect, for example, an oxygen decrease as a result of cardiac arrest even in the absence of a detectable pulse. In this context, detectable pulse may comprise a weak pulse or no pulse. In this regard, system 100 may be considered as having a sensitivity improvement over conventional oximetry devices.

Broad-spectrum oximetry probe 102 in this embodiment further comprises a complementary spectrometer 108 (or sensor) operable to acquire a complementary optical signal from the user body region so to digitally capture complementary respective spectral responses. The spectrometer and the complementary spectrometer 108 in this example are arranged at different distances from the broad-spectrum light source 106: the spectrometer 108 located 2 cm from the light source 106 (forming a "close sensor"), and the complementary spectrometer 108 located 3.5 cm from the broad-spectrum light source 106 (forming a "far sensor").

As reflected in FIGS. 11 and 12 and as discussed below, generally, a greater number of respective spectral responses spectrally resolved by the spectrometer 108 and complementary spectrometer 108 (although such may be obtained by only a single spectrometer in other embodiments) may result in increased resolution of temporal variations over time. Naturally, increased resolution in turn reflects a decreased noise-to-signal ratio, facilitating identification of temporal variations by the digital data processor 112. Notably, one drawback of conventional pulse oximeters is determining regional blood oxygen measurements, which typically relies on trending (taking averages over time for predefined wavelengths). Conventional regional blood oxygen measurements are therefore not immediately sensitive to increases or decreases in blood oxygen. In the context of cerebral oximetry, therefore, regional pulse oximeters do not offer the temporal resolution necessary to assist the emergency responder administering CPR. However, system 100 may not rely on trending. In particular, as a result of the specific responses analysed by system 100 (which may be either distinct spectral wavelength regions or a broad-range), the sensitivity of system 100 is increased and greater temporal resolution is obtainable, specifically allowing individual physiological events to be identified. Such temporal resolution is necessary, for example, to assist administration of CPR. It is to be appreciated, nonetheless, that a lesser number of respective spectral responses (i.e. lesser wavelengths) utilised by system 100 may still attain a suitable level of sensitivity or resolution to identify temporal variations in oxygen levels at the user body region, provided the lesser number of respective spectral responses are strategically selected. In particular, the lesser number of respective spectral responses may be strategically selected to reflect oxygen levels, or more particularly, concentration of oxygen-related blood-borne chromophores.

The oxygen levels temporally monitored by broad-spectrum oximetry system 100 at the user body typically refers to oxygen saturation of tissue, blood, or other components at the user body region. As such, in this particular embodiment, the blood-borne chromophores probed for by probe 102 comprise a combination of: deoxyhemoglobin, oxyhemoglobin, and dissolved oxygen. Thus, system 100 in this embodiment is specifically designed to monitor oxygen levels at the user body region. Notably, the temporal variations identified by system 100 may be further representative of blood volume at the user body region in real time. In particular, even if hemoglobin is not oxygenated, it may still be possible with system 100 to detect blood volume based on deoxyhemoglobin probed. Increased blood volume in the form of deoxyhemoglobin will lead to increased absorption and thus temporal variations therein may be identifiable by the digital data processor 112. Furthermore, an increase in blood volume at the user body region may have a physiological effect of increased blood pressure which in turn, may lead to increased oxygen levels by mere diffusion to the user body area. Thus, relating temporal variations with blood volume may provide additional useful data to clinicians or emergency responders.

Probe 102 is non-invasive. Typical user body regions for monitoring include a cerebral region and a wrist region, but skilled technicians will appreciate that system 100 may be attached and utilised to determine oxygen levels at any body region.

System 100, in this embodiment, is integrated into a wearable oximeter device suited to the particular body region to which it is to be attached. To facilitate a user viewing the temporal variations, system 100 further comprises an electronic communications interface 130 in communication with the digital data processor 112 to receive and display the temporal variations with the resolution allowing individual physiological event identification in real time. The temporal variations displayed to the user in real time on the electronic communications interface 130 allows immediate visible notification of the temporal variation. This may be accompanied by an audible notification in some embodiments which may be useful, for example, where a negative user outcome is predicted by system 100, such as predicted injury or death, and immediate action is advised.

Now turning to FIGS. 7 to 10, an exemplary set of measurements and plots acquired using the above exemplary embodiment of broad-spectrum oximetry system 100 for temporally monitoring oxygen levels at the user body region, will be discussed.

In the experimental setup of system 100, the user was placed under hypoxic conditions, simulating an expected condition of the user after pulse and breathing have ceased. Naturally, in such hypoxic conditions, the oxygen levels of the user are decreased (and oxygen reaching tissues is decreased) and a pulse would be undetectable by conventional pulse oximeters. In this regard, simulating cardiac arrest was not necessary since system 100 does not rely on a pulse for data acquisition, as described. Removal of the pulse signal would affect some frequency variations in the nominal pulse range (60 bpm to 120 bpm) but would otherwise not alter the overall level of transmission at each wavelength. To place the user under hypoxic conditions, the user inhaled a mix of hypoxic air (95% $N_2$, 5% $O_2$) for 4 minutes, thereby reducing oxygen levels as much as possible until a quasi-stable level was reached. For "large" bolus tests, as detailed further below, a large oxygen bolus (at higher $O_2$ concentration) was introduced at the 4 minute mark, followed by a second large oxygen bolus at the 8 minute mark, with a return to normal air breathing at the 12 minute mark. For "small" bolus tests, a smaller oxygen bolus was introduced at the 4 minute mark, followed by a second at the 7 minute mark, with a return to normal air breathing at the 10 minute mark. Both large and small boluses were used such that a higher concentration of $O_2$ was inhaled by the user to simulate the $O_2$ that would be introduced into the lungs through artificial breathing, for example. More details are provided below. Specifically, in separate experiments, the user inhaled a higher concentration of oxygen, called a large oxygen bolus, and a lower concentration of oxygen, called a small oxygen bolus, whilst spectral transmission data was obtained via probe 102. All spectra were acquired by integrating the at-sensor intensity over a 100 ms interval at 1 Hz acquisition frequency. To exemplify use of system 100 at different user body regions, in FIGS. 7 and 8 probe 102 was fixed to a cerebral region (forehead) of the user, whilst in FIGS. 9 and 10 probe 102 was fixed to a wrist region of the user.

In FIGS. 7 to 10, the spectral transmission data consists of at-sensor intensities, acquired as described, shown in arbitrary detector units. In these figures, a first set of lines show the spectral transmission data obtained whilst the user was in the hypoxic state, whilst a second set of lines show the spectral transmission data obtained after administration of an oxygen bolus (whether large or small), thereby illustrating the temporal variation in oxygen levels caused as a result of the oxygen bolus.

Figure 7:
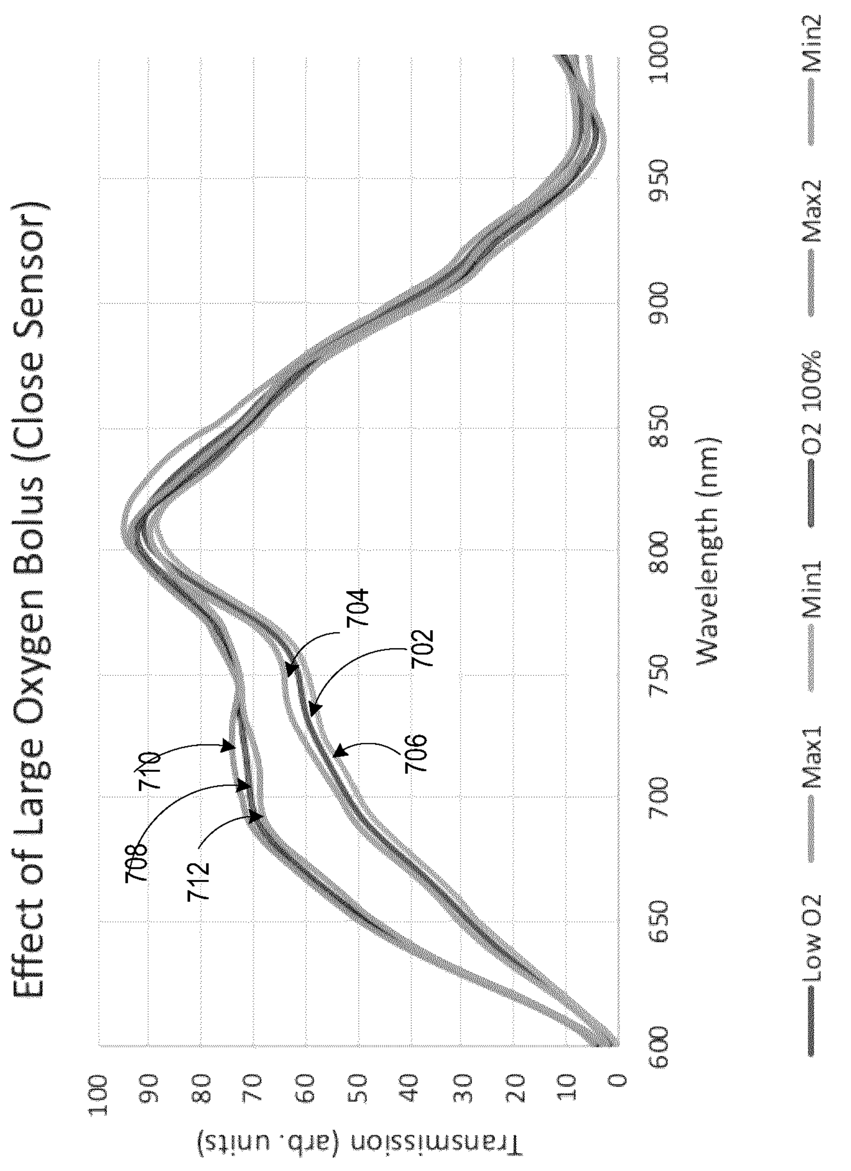
FIG. 7 is an exemplary plot of an average change of spectral readings taken by a close sensor positioned at a cerebral region, when a user in hypoxic conditions is administered a large oxygen bolus, reflected as transmission at different wavelengths, in accordance with one embodiment, wherein the close sensor in this example is a closest one of two sensors positioned at different distances from a probing light source.
Figure 8:
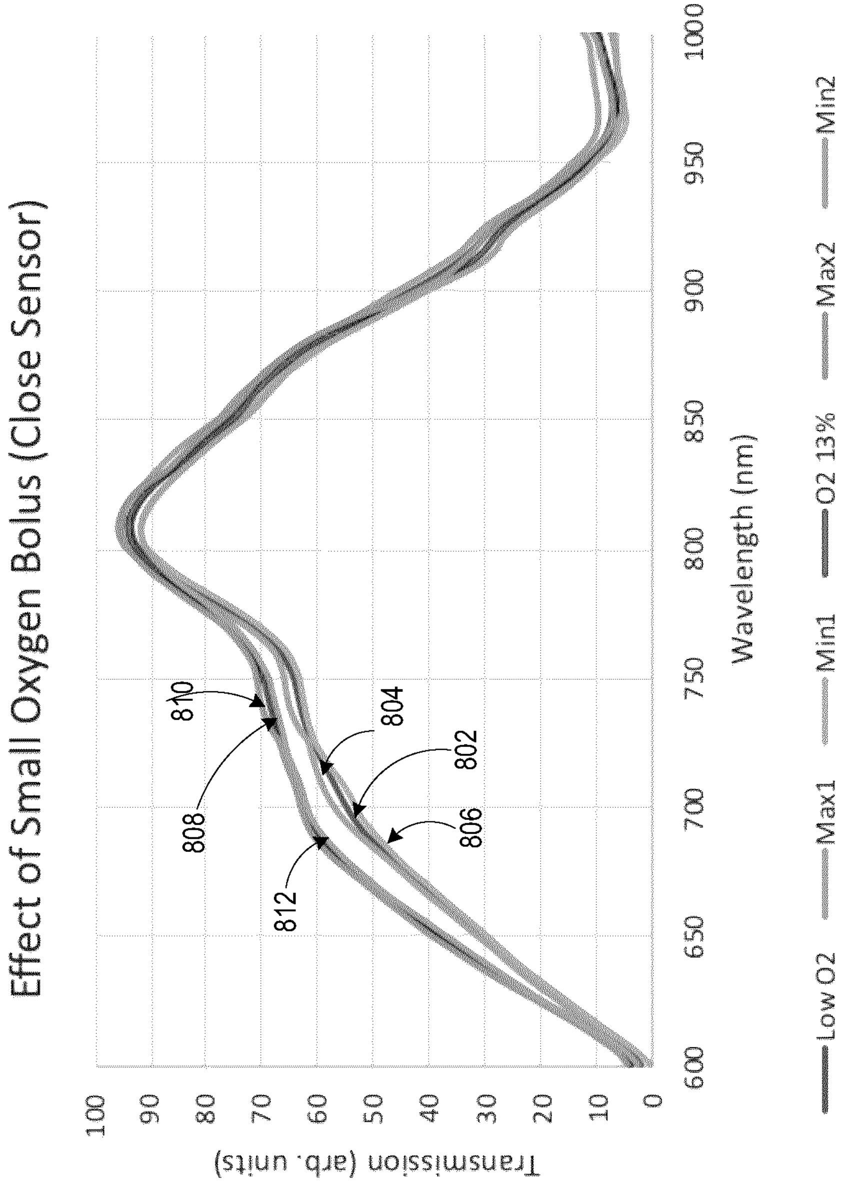
FIG. 8 is an exemplary plot of an average change of spectral readings taken by the same close sensor as in FIG. 7, when the user in hypoxic conditions is administered a small oxygen bolus, reflected as transmission at different wavelengths, in accordance with one embodiment.

FIGS. 7 and 8 show respective plots of an average change of spectral transmission readings taken at a cerebral region when a user in hypoxic conditions is administered a large oxygen bolus (FIG. 7) and a small oxygen bolus (FIG. 8), respectively. Specifically, in FIGS. 7 and 8, the dark blue lines 702, 802 ("Low O2") show an average spectra (comprised of a total of 10 spectra) measured over 10 seconds whilst the user was in the hypoxic state, just before a time of 4 minutes (between 4 mins:40 seconds to 4 mins:50 secs); the orange lines 704, 804 ('Max1') show maximum values for each wavelength at this time; and the grey lines 706, 806 ("Min1") show minimum values for each wavelength at this time. The red lines 708, 808 ("O2 100%") show an average spectra over a 5 second period just after the oxygen bolus (smaller or large) was introduced, at the approximate range between 4 mins:10 secs to 4 mins:15 secs; the light blue lines 710, 810 ("Max2") show maximum values for each wavelength at this time; and the green lines 712, 812 ("Min2") show minimum values for each wavelength at this time.

To obtain the transmission data of FIG. 7, the user inhaled the hypoxic mix, as described, for 4 minutes before inhaling a large oxygen bolus, comprised of two normal breaths of 100% $O_2$. Thereafter, the user continued to inhale the hypoxic mix. To obtain the transmission data of FIG. 8, the user inhaled the hypoxic mix, as described, for 4 minutes before inhaling a small oxygen bolus, comprised of a single breath of another hypoxic mix, representing approximately half the oxygen content found in normal air and comprised of 13% $O_2$ and 87% $N_2$. In both FIGS. 7 and 8, the effect of the oxygen bolus on spectral transmission at the cerebral region can be observed, specifically increasing overall transmission in the 600 nm to 770 nm range. Furthermore, comparing FIGS. 7 and 8 reflects, inter alia, that a larger oxygen bolus exhibits greater spectral transmission as compared to a smaller oxygen bolus, corresponding to an increased oxygen concentration or saturation at the cerebral region.

Figure 9:
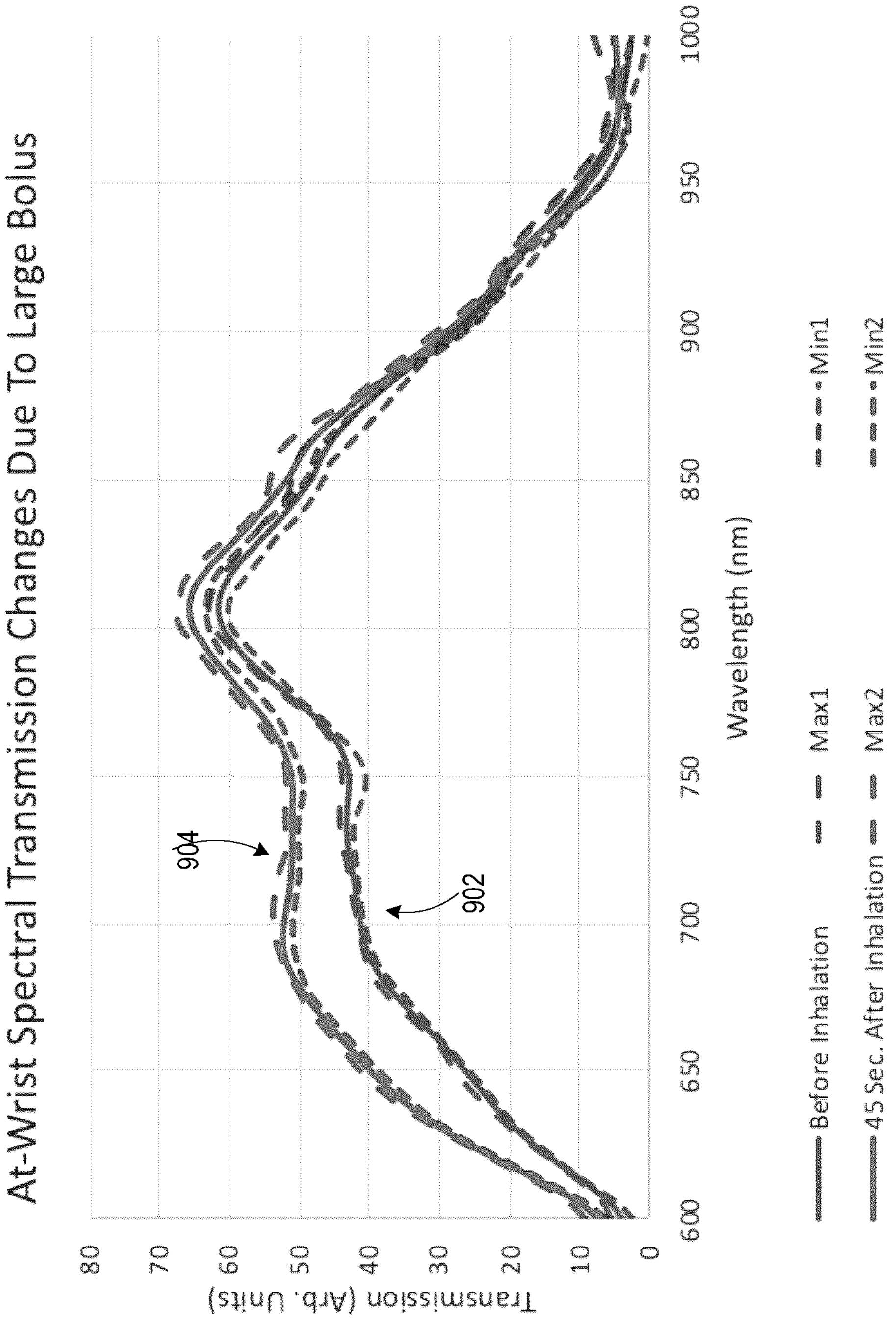
FIG. 9 is an exemplary plot of an average change of spectral readings taken by the same close sensor as in FIG. 7, but when positioned at a wrist region, when a user in hypoxic conditions is administered a large oxygen bolus, reflected as transmission at different wavelengths, in accordance with one embodiment.
Figure 10:
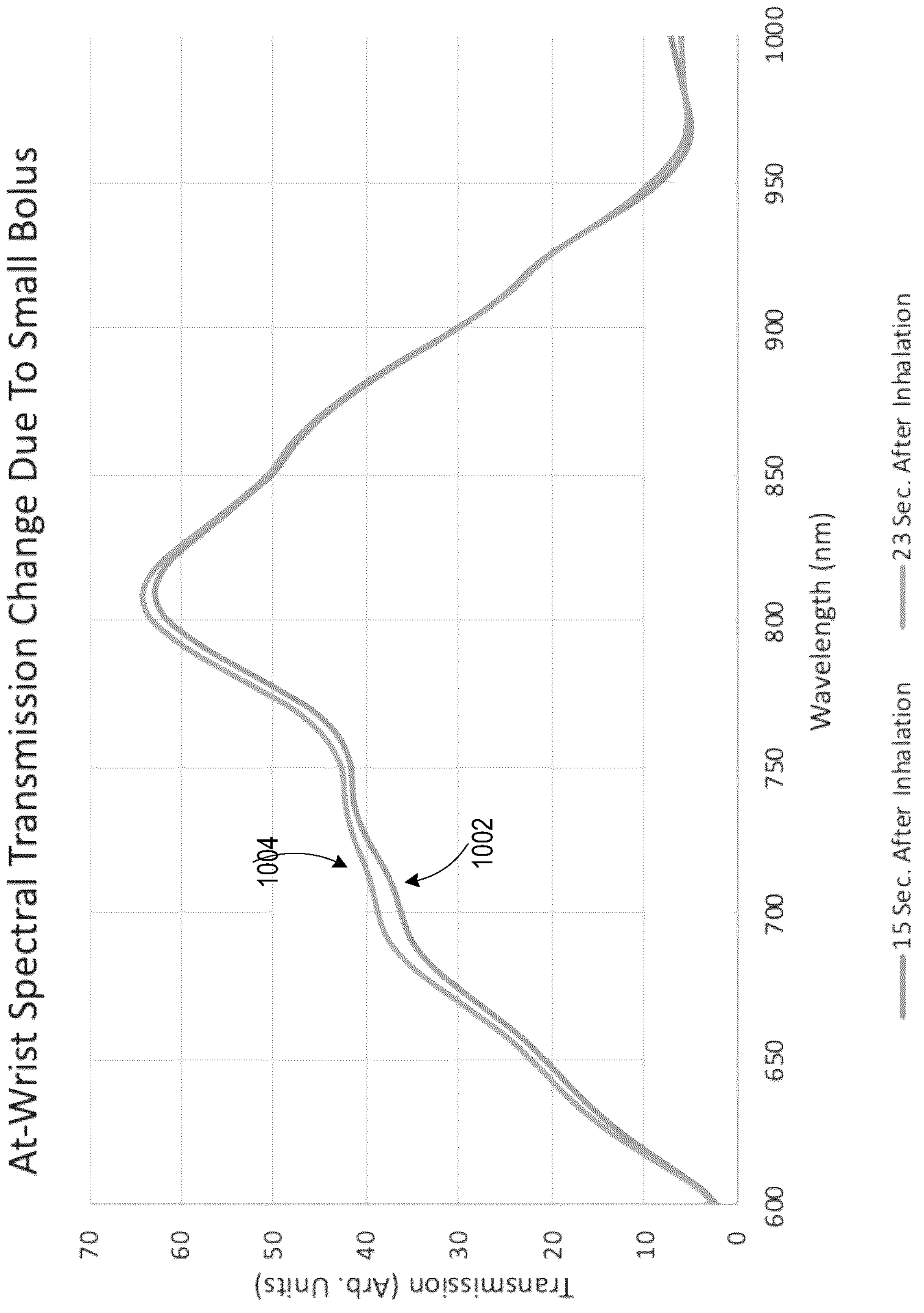
FIG. 10 is an exemplary plot of an average change of spectral readings taken by the same close sensor as in FIG. 9, when positioned at a wrist region, when a user in hypoxic conditions is administered a small oxygen bolus, reflected as transmission at different wavelengths, in accordance with one embodiment.

FIGS. 9 and 10 show respective plots of an average change of spectral transmission readings taken at a wrist region when a user in hypoxic conditions is administered a large oxygen bolus (FIG. 9) and a small oxygen bolus (FIG. 10) respectively. The spectra are averages over 10 or 5 second periods. In FIG. 9, the blue lines 902 show the spectral transmission data obtained whilst the user was in the hypoxic state (i.e. before inhalation) and the red lines 904 show the spectral transmission data obtained about 45 seconds after the large oxygen bolus. In turn, solid lines reflect an average transmission values obtained and broken lines reflect respective maximum and minimum transmission values obtained. In FIG. 10, the orange line 1002 shows the spectral transmission data obtained about 15 seconds after the small oxygen bolus and grey line 1004 shows spectral transmission data obtained about 23 seconds after the small oxygen bolus.

To obtain the transmission data of FIG. 9, the user inhaled the hypoxic mix, as described, for 4 minutes before inhaling a large oxygen bolus, comprised of two normal breaths of 100% $O_2$. Thereafter, the user continued to inhale the hypoxic mix. To obtain the transmission data of FIG. 10, the user inhaled the hypoxic mix, as described, for 3 minutes in this test, before inhaling a small oxygen bolus, comprised of a single breath of another hypoxic mix, representing approximately half the oxygen content found in normal air, comprised of 13% $O_2$ and 87% $N_2$. Again, both FIGS. 9 and 10 reflect the effect of the oxygen bolus on spectral transmission at the wrist region, specifically increasing overall transmission in the 600 nm to 750 nm range. In the case of the large oxygen bolus (FIG. 9), the spectral transmission data obtained shows a similar increase in transmission in the 600 nm to 750 nm range due to the reduced deoxyhemoglobin (thus decreased absorbance). However, the increase due to the large oxygen bolus shown in FIG. 9 at the wrist region was observed at a significantly longer time (about 40 seconds) than the sharp increases at the cerebral region shown in FIG. 7, which were observed at about 10 seconds after inhalation.

Furthermore, in FIG. 10, the changes due to the small oxygen bolus are significantly smaller than those due to the large oxygen bolus (FIG. 9). To highlight the increase in the case of the small oxygen bolus at the wrist, the changes in spectra arising from the small oxygen bolus after about 20 seconds were compared with spectra at about to 15 seconds after inhalation to illustrate the difference.

Notably, the increases in transmission observed in FIGS. 9 and 10 (wrist region) are less pronounced as compared to FIGS. 7 and 8 (cerebral region). Furthermore, comparing FIGS. 9 and 10 again reflects, inter alia, that a larger oxygen bolus exhibits greater spectral transmission as compared to a smaller oxygen bolus, corresponding to an increased oxygen concentration or saturation at the wrist region.

Another observable distinction between the FIGS. 7 and 8 (cerebral region) and FIGS. 9 and 10 (wrist region) is that the latter both exhibit a significantly longer delay before the increase in spectral transmission (corresponding to oxygen concentration) can be observed from the plot. This observable difference may be attributed, at least in part, to the decreased volume of blood present at the wrist region (FIGS. 9 and 10), comparative to the volume of blood present at the cerebral region (FIGS. 7 and 8). Alternatively, or in addition thereto, the observable difference may be attributable to an oxygen transport delay, corresponding to the time taken for newly oxygenated blood to reach the respective body regions. As a consequence of anatomy and blood flow, a delay between oxygen diffusion or uptake at the lungs of the user and delivery of oxygenated blood to the wrist may be longer than delivery of oxygenated blood to the cerebral region. This aspect is discussed further below.

FIGS. 7 to 10 demonstrate specifically that relatively small amounts of oxygen variation, specifically increases here, can be detected by this embodiment of system 100 using broad range spectral transmission data. In particular, a significant increase in transmission in the 600 nm to 750 nm wavelength is detected just after an oxygen bolus (regardless of size) is introduced in the lungs. The increase in transmission (or decrease in absorption) may be explained, at least partially, by a decrease in deoxyhemoglobin which is known by skilled technicians to show strong absorption in that range. Furthermore, as mentioned, the small oxygen bolus (FIGS. 8 and 10) shows significantly less increase in the 600 nm to 750 nm wavelength as compared to the large oxygen bolus (FIGS. 7 and 9), which is to be expected considering the lesser oxygen administered. Skilled technicians will appreciate that relatively small oxygen level decreases would be detectable by system 100 with a similar sensitivity and accuracy.

Figure 11:
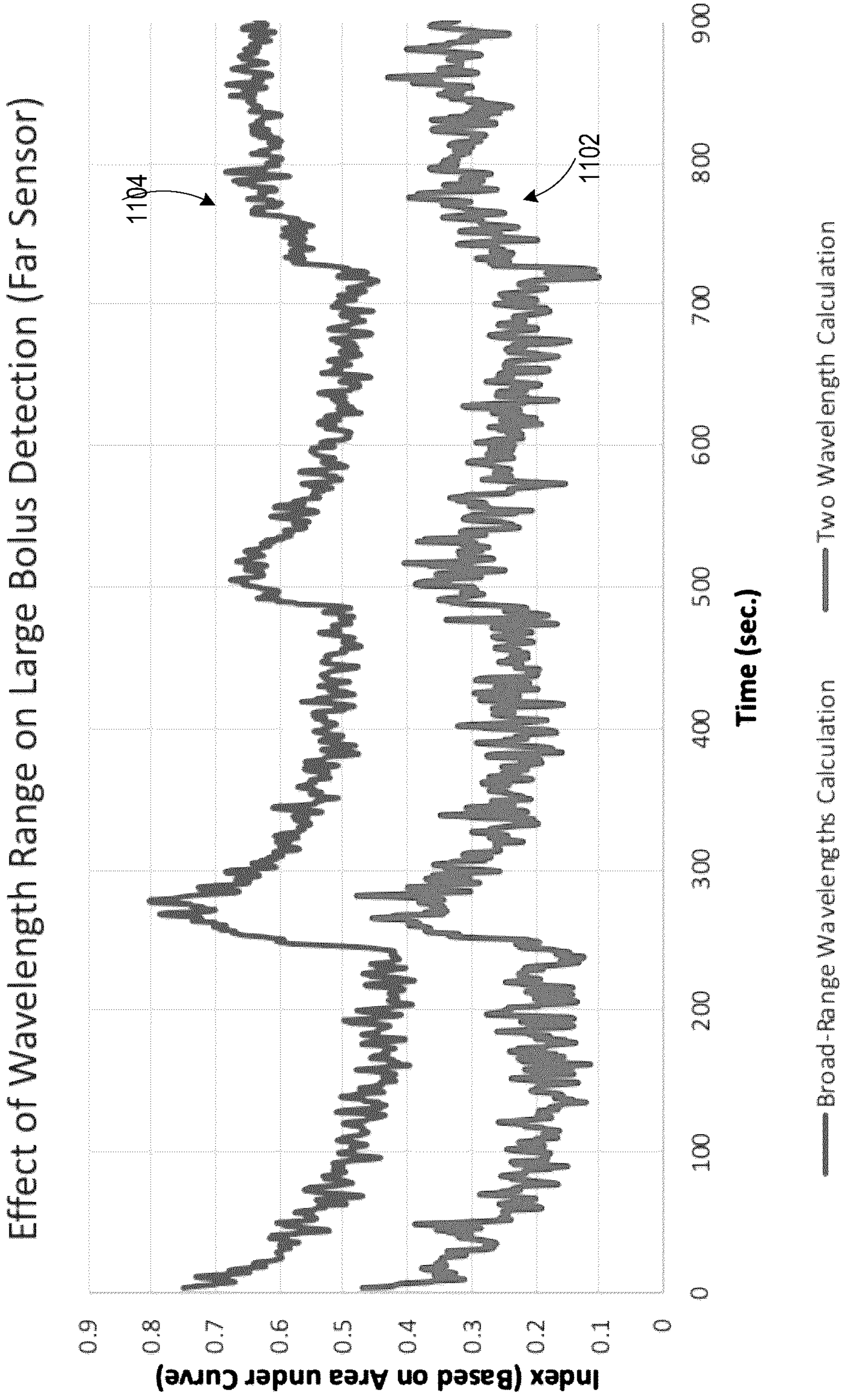
FIG. 11 is an exemplary plot of an index obtained from similar test data as portrayed and exemplified in FIG. 7 for a large oxygen bolus, in this example, however, obtained using a furthest sensor from the probing light source, wherein the index in this example is defined as an area under the curve (AUC) above and below 800 nm is obtained and plotted over time using two wavelengths as compared with a broad-range of wavelengths, in accordance with different embodiments.
Figure 12:
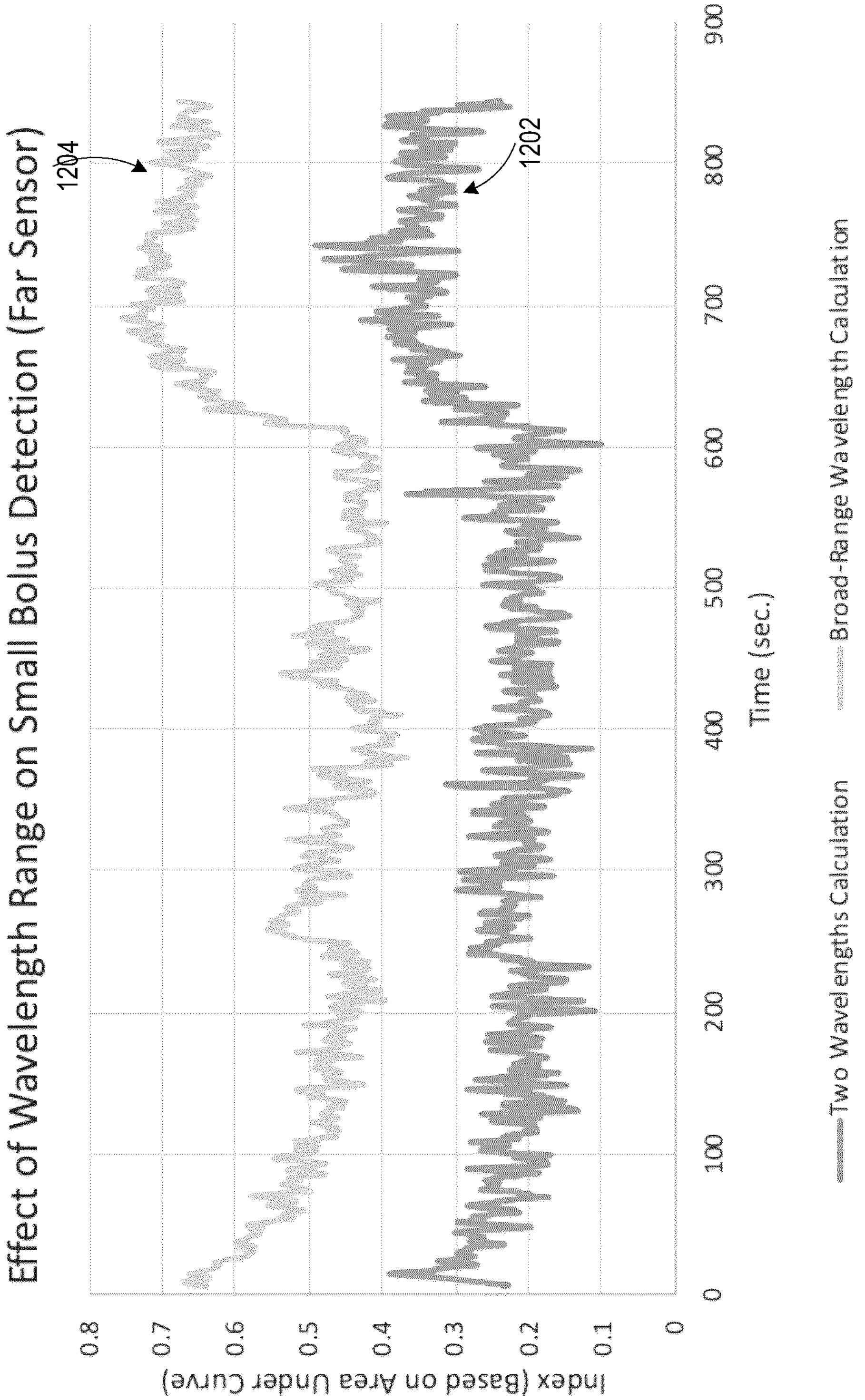
FIG. 12 is an exemplary plot of an index obtained from similar test data as portrayed and exemplified in FIG. 8 for a small oxygen bolus, in this example, however, again obtained using a furthest sensor from the probing light source, wherein the index in this example is again defined as in FIG. 11 and compared for two wavelengths and a broad-range of wavelengths.

With reference to FIGS. 11 and 12, an exemplary set of indices calculated based on measurements and plots acquired in FIGS. 7 and 8 at the cerebral region, will be discussed.

In this exemplary embodiment, the indices calculated in FIGS. 11 and 12 are based on the total area under the curves of FIGS. 7 (large oxygen bolus) and 8 (small oxygen bolus), respectively, derived based on the ratio of the area under the spectral transmission curve at each timestamp. Thus, these indices reflect simple area under the curve (AUC) indexes. To highlight realistic conditions that would be suboptimal, data is shown for the far sensor from the light source 106. In both FIGS. 11 and 12, the effect of the number of wavelengths utilised in the calculation of the area (top vs bottom curves) is illustrated. In one instance (two wavelength calculation), the index is calculated as a ratio of the area under the curve between 650 nm and 655 nm to the area under the curve between 810 nm and 815 nm. This required 2 data points for each area (5 nm spacing) and has a range similar to existing oximeters. In FIGS. 11 and 12, this two-wavelength index is indicated with red line 1102 and orange line 1202, respectively. In the other instance (broad range wavelength calculation), the index is calculated using a much higher number of wavelengths to obtain the area under the curve between 650 nm and 750 nm to the area under the curve between 800 nm and 950 nm. In FIGS. 11 and 12, this broad range-wavelength index or multi-wavelength index is indicated with blue line 1104 and yellow line 1204, respectively.

As blood is oxygenated by the oxygen bolus (large or small), the levels of deoxyhemoglobin decrease and thus the transmission in the 650 nm to 750 nm will increase, thereby increasing the index value. In both FIGS. 11 and 12, system 100 can readily detect the oxygen boluses at 4 minutes and 7 or 8 minutes (corresponding with the second breath taken around that time in different tests). The larger oxygen bolus (FIG. 11) shows a sharper increase, whereas the smaller oxygen bolus (FIG. 12) shows a less sharp increase, as expected due to the higher oxygen content.

Figure 13:
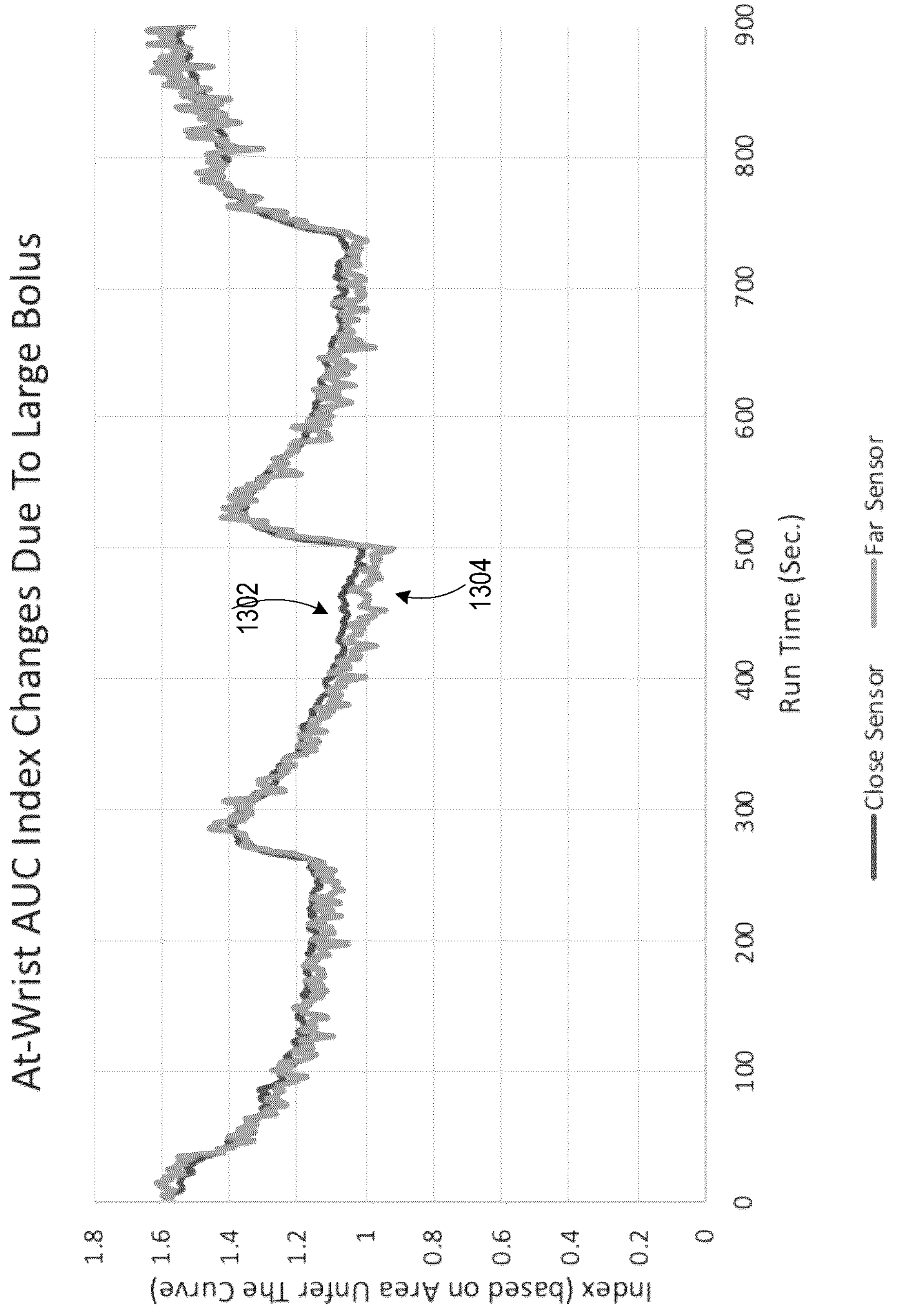
FIG. 13 is an exemplary plot of an area under curve (AUC) index, as defined for example for FIG. 11, for test data as obtained for example as defined for a large oxygen bolus in FIG. 9, comparing this index as calculated for sensors at the wrist region that are located closest and furthest form the probing light source.
Figure 14:
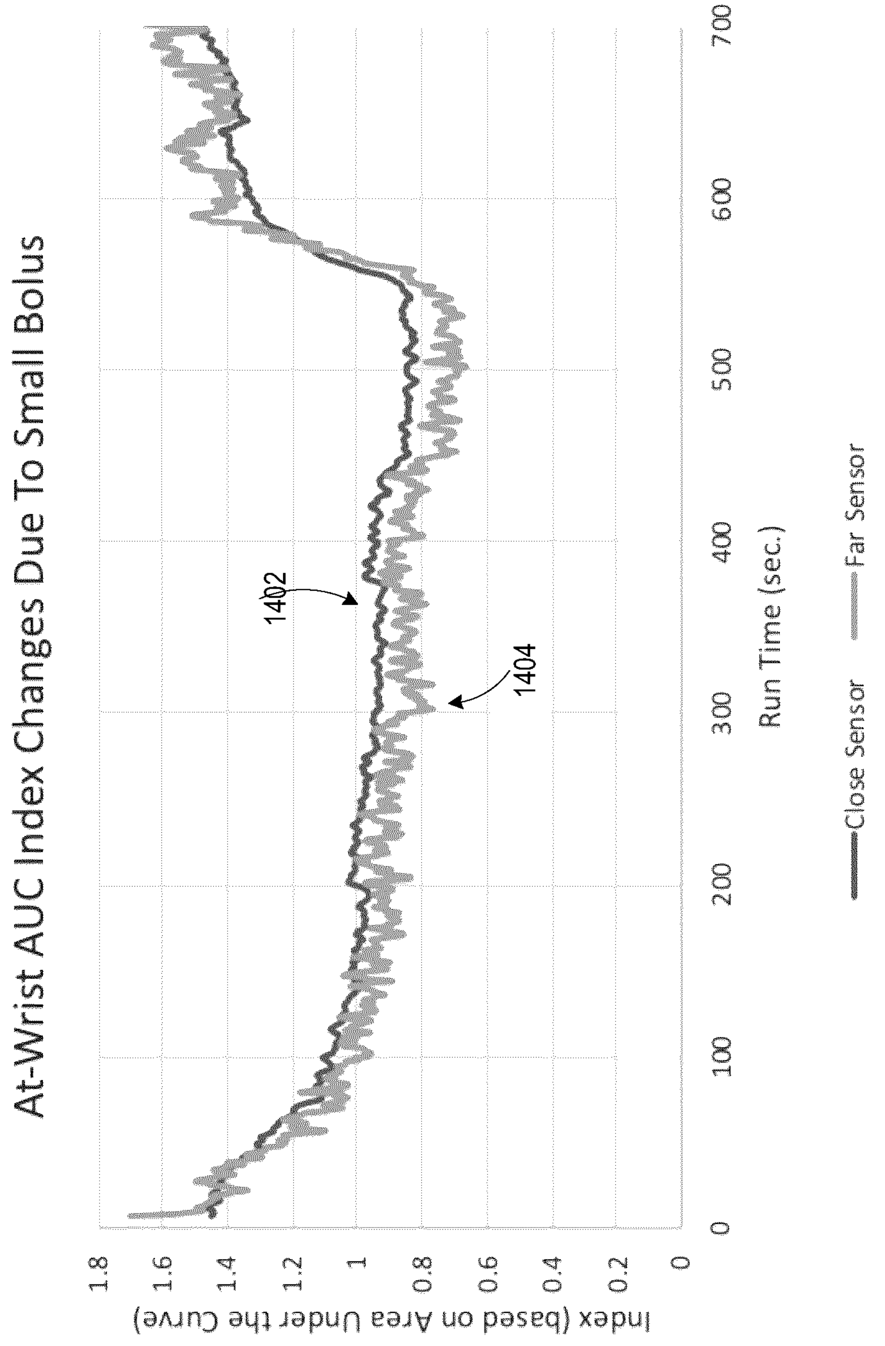
FIG. 14 is an exemplary plot of an AUC index, as defined for example for FIG. 11, for test data as obtained for example as defined for a small oxygen bolus in FIG. 10, comparing this index as calculated for sensors at the wrist region that are located closest and furthest from the probing light source.

With reference to FIGS. 13 and 14, an exemplary set of indices calculated based on measurements and plots acquired in FIGS. 9 and 10 will be discussed. FIGS. 13 and 14 again reflect simple AUC indices based on the measurements obtained at the wrist region for the large oxygen bolus (FIG. 13) and the small oxygen bolus (FIG. 14), respectively. FIGS. 13 and 14 show AUC indices based on measurements obtained from the close sensor 108 with blue lines 1302, 1402, and the far sensor 108 with orange lines 1304, 1404.

The difference in time required for temporal variations (specifically increases) to be observed between the cerebral region (as shown in FIGS. 11 and 12) and the wrist region (as shown in FIGS. 13 and 14) can further be observed using the simple AUC index, as discussed. FIGS. 11 and 13 both show the variations in the AUC index resulting from large oxygen boluses inhaled at 4 minutes. However, as mentioned, the onset of the increases is observed at different times: for the cerebral region (FIG. 11), the onset is at about 2 seconds after inhalation, or within a few seconds considering potential timing errors. In FIG. 13, on the other hand, the onset is at about 20 seconds after inhalation. Again, this delay in onset (or oxygen transport delay) may be attributed to the anatomical distance between the lungs where oxygenation occurs and delivery of oxygenated blood to the respective body regions, with the cerebral region receives oxygenated blood prior to the wrist region, for example.

FIG. 14 shows the same AUC index for the small oxygen bolus at the wrist region. The small oxygen bolus at 3 minutes and 6 minutes can be seen again at about 20 seconds after inhalation, at about 200 seconds and at about 380 seconds. However, the increase can only be barely observed with the sensor 108 closest to the source 106 and is very difficult to make out with the further complementary sensor. Referring back to the index obtained for the cerebral region, however, the small oxygen bolus could be more easily detected (see FIG. 8). Skilled technicians will appreciate that it would be challenging to detect in real time (or even in quasi-real time) the type of variation (specifically increase) seen in FIG. 14 arising from the small oxygen bolus. As such, in some embodiments, system 100 may compensate for small temporal variations by trending or averaging the values over time. In such embodiments, trending or averaging values over time may reduce capability of detecting the exact onset or occurrence of individual boluses, in an effort to increase identification of such temporal variations.

Figure 15:
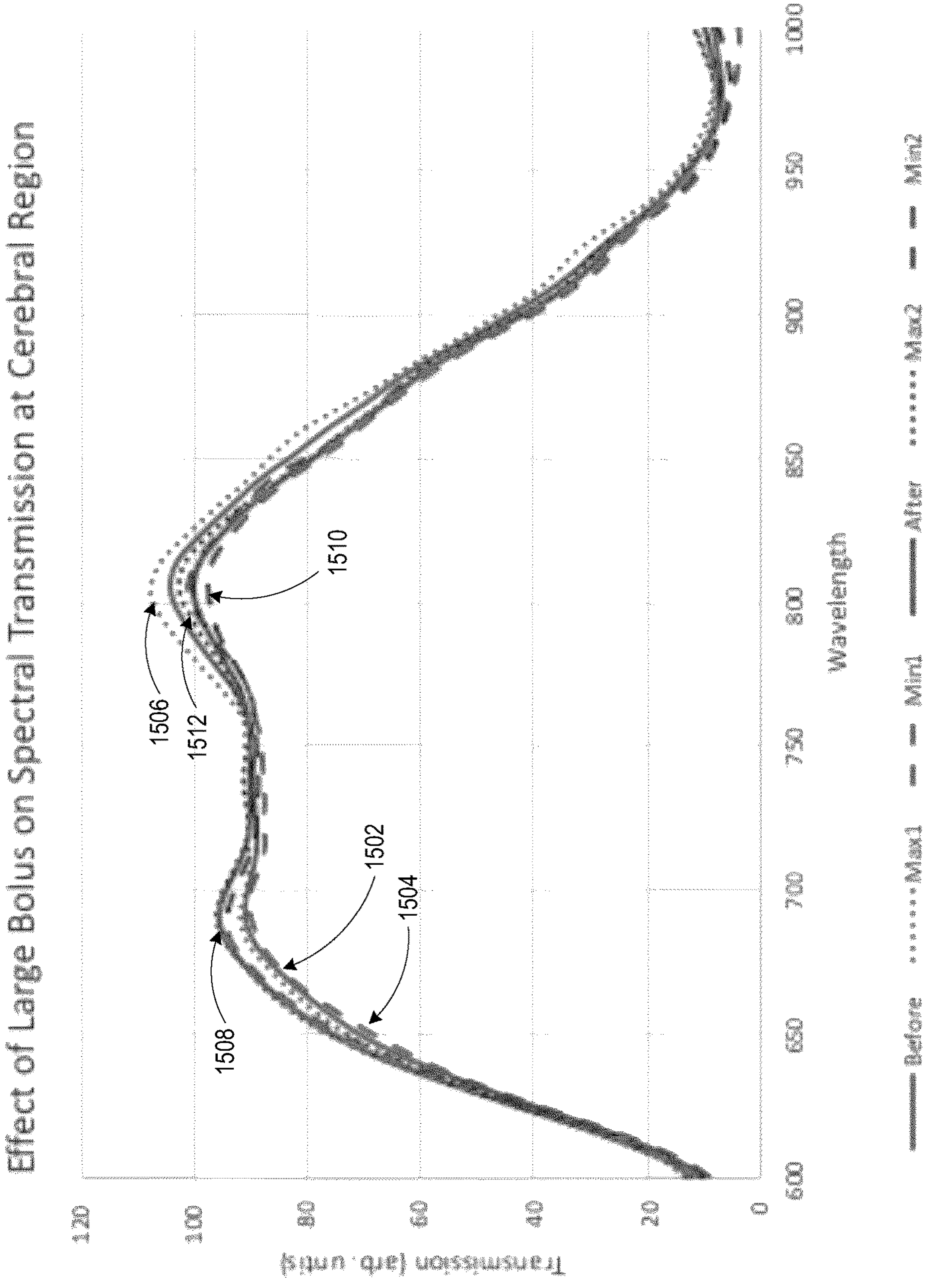
FIG. 15 is an exemplary plot of minimum and maximum spectral readings in a cerebral region for periods before and after inhalation of a large oxygen bolus (100% $O_2$) by a user in a normoxic state (i.e. otherwise breathing normal ambient air—21% $O_2$, for a prolonged period); "before"=10 spectra acquired from t=2 min:45 sec to t=2 min:55 sec; "after"=5 spectra from t=3 min:30 sec to t=3 min:35 sec, in accordance with one embodiment, showing operability of the herein described embodiments under normobaric normoxic conditions.
Figure 16:
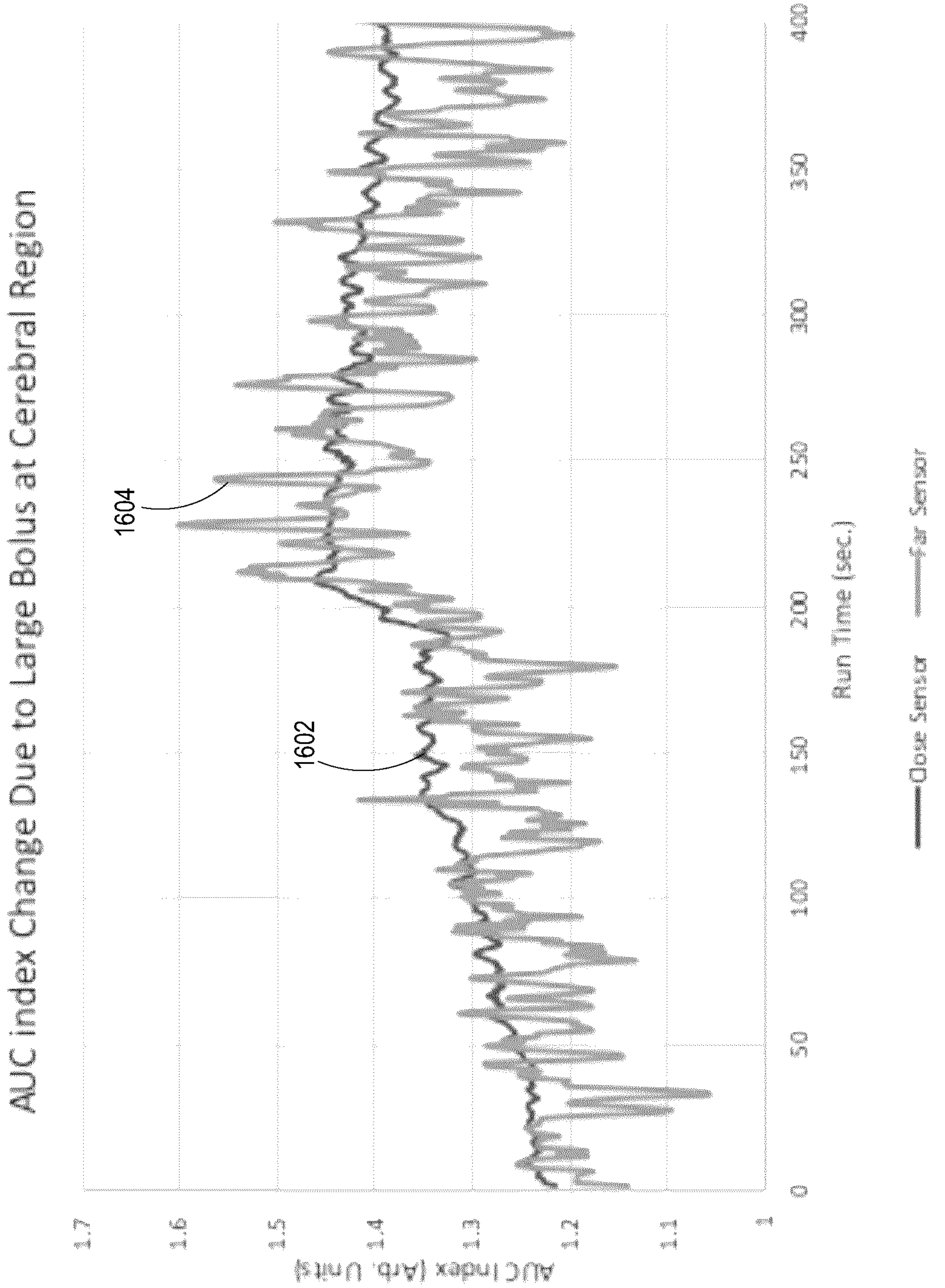
FIG. 16 is an exemplary plot of a change in an AUC index, as defined above, as calculated from data as acquired and discussed with reference to FIG. 15 for a closest and furthest sensor from a probing light source, and showing a noticeable increase at t=3 min:9 sec.

With reference now to FIGS. 15 and 16, and in accordance with one embodiment, further results are obtained, in this example, using a broad-spectrum oximeter as described herein, for a user in a normoxic state, that is a user exposed to normal breathing air (i.e. 21% $O_2$) for a prolonged period of time. These results provide a comparative use of the herein described solutions to those presented above for a user in a hypoxic state to show that these solutions may equally be applied to temporal oxygen bolus detection under normal breathing/oxygen conditions as well as under abnormal conditions.

In this particular test, normal air was inhaled for 3 minutes. At t=3 minutes, a large bolus of oxygen was created by inhaling two breaths of 100% Oxygen, after which there was a return to normal air.

In FIG. 15, an exemplary plot of minimum and maximum spectral readings in a cerebral region for periods before and after inhalation of a large oxygen bolus (100% $O_2$) by a user in a normoxic state are illustrated. The solid blue "before" spectrum (1502) represents the 10 spectra acquired from t=2 min:45 sec to t=2 min:55 sec, with minimum and maximum spectra shown as blue dashed (1504) and doted (1506) spectra, respectively, whereas the solid red "after" spectrum (1508) represents the 5 spectra acquired from t=3 min:30 sec to t=3 min:35 sec, with minimum and maximum spectra shown as blue dashed (1510) and doted (1512) spectra, respectively. The increase in transmission below about 800 nm and the decrease above 800 nm is consistent with results previously obtained. Here however, the oxygen content introduced into the body is significantly lower than the tests previously shown where 100% $O_2$ was inhaled for longer periods of time. This test shows that there herein-described solutions can also detect boluses even under normobaric normoxic conditions.

FIG. 16 is an exemplary plot of a change in an AUC index, as defined above, as calculated from data as acquired and discussed with reference to FIG. 15, for a closest sensor (see line 1602) and furthest sensor (see line 1604) from a probing light source, and showing a noticeable increase at t=3 min:9 sec. Two observations are notable for these results. First, the rate of index (and $O_2$ content) decrease back to normal levels is much less than in tests under hypoxic states. This can be explained in part due to 1) the relatively reduced $O_2$ content in the volume of the bolus inhaled relative to the oxygen already in the body, and 2) the body's increased need for oxygen when in hypoxic states relative to its reduced need in normal conditions (which will affect heart rate and blood flow for example). Second, the onset of the increase in $O_2$ at the cerebral region takes more time than in tests under hypoxic conditions. Again, this can be explained in part by the two reasons discussed just above.

As illustrated, therefore, using a greater number of wavelengths, as system 100 can do, provides improved resolution at least in the form of clearer definition of the sharp increase in the large oxygen bolus. In the small oxygen bolus, the increase, while detectable using the calculated index using only a few wavelengths, becomes clearer for embodiments employing a fuller spectrum analysis. As mentioned, the small oxygen bolus simulates the scenario to be expected in real life, when resuscitation is performed using conventional air with suboptimal volumes of air forced into the user's lungs (resulting in small oxygen boluses). As shown herein, such temporal variations may be detected using embodiments employing two, three or more distinct wavelengths/regions, and increasingly so when employing a broad-spectrum light source and sensor. Indeed, system 100, which can utilise a broad range of wavelengths in an index calculation, can provide improved resolution and/or less noise such that probe 102 can be more accurately or effectively utilised for example, to reflect smaller oxygen boluses in critical real life scenarios.

Figure 17:
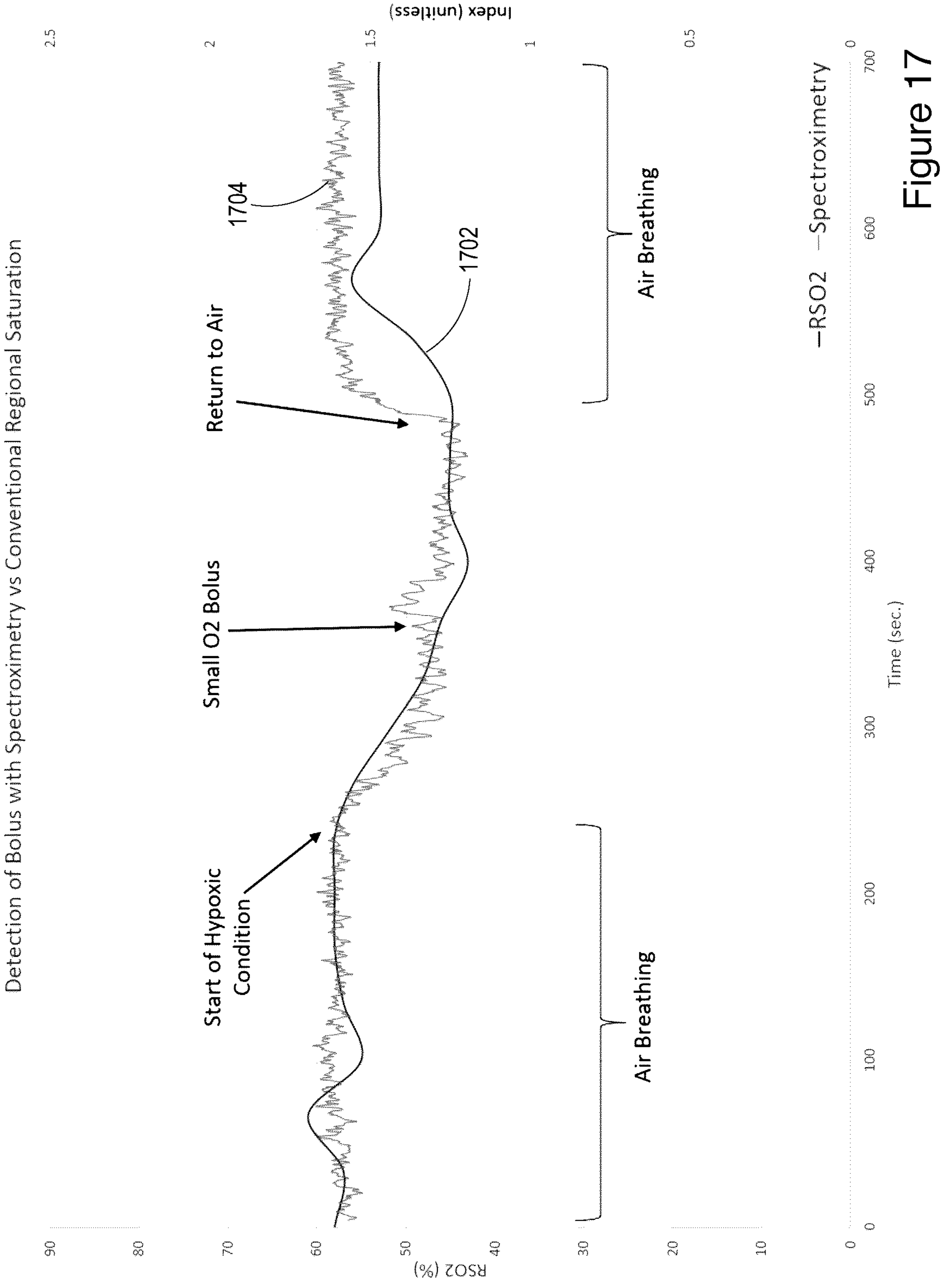
FIG. 17 is an exemplary plot of data which compares, in a single test, a conventional regional oximeter (which outputs regional saturation (RSO2) data) with an exemplary broad-spectrum oximetry device (where output was defined, for exemplary purposes only, as an index calculated based on the area under the curve (AUC) of wavelengths above and below 800 nm), in accordance with one embodiment of the present disclosure, respectively tested to detect delivery of a small oxygen bolus to an individual in a hypoxic condition, which illustrates, for example, that whilst conventional regional oximeters cannot detect individual small boluses, the exemplary broad-spectrum oximetry device of the present disclosure is able to detect such small boluses with observable resolution.

With reference now to FIG. 17, and in accordance with one embodiment, comparative results were obtained using a broad-spectrum oximeter as described herein (i.e. spectroximetry), and conventional cerebral (regional) oximeter, specifically a well-established cerebral oximetry device (INVOS 5100C) which is considered a standard in the field of oximetry devices. These comparative results, taken during a single test, illustrate at least the improved resolution (or feature discrimination) offered by the broad-spectrum oximeter as described herein, relative to conventional regional oximeters, such as the INVOS conventional cerebral oximeter, as will be described below.

In this particular embodiment, the broad-spectrum oximeter obtained and/or resolved all wavelengths in a range of 600 nm to 1000 nm (not just a select few) and the data displayed represents an index calculated based on the ratio of the Area Under the Curve (AUC) of the wavelengths above 800 nm (i.e. 800 or 801 nm to 1000 nm) to those under (i.e. 600 nm to 799 nm or 800 nm). A simple 2-value ratio was used for comparison purposes only, with ratios based on 2 wavelengths, such as that used by the conventional INVOS cerebral oximeter. It is to be appreciated that more complex and effective indices based on the high resolution wavelengths can be designed, as described herein, all of which are intended to fall within the scope of the present disclosure.

To obtain this comparative data, the test consisted of detecting a small rise of oxygen levels in cerebral blood during significant hypoxia, to simulate conditions of CPR given to a patient after cardiac arrest. One purpose of the test was thus to detect a very small increase in $O_2$ level reaching the cerebral region, that could be representative of the small level of $O_2$ introduced through assisted breathing during CPR with chest compressions. In the test, the individual first breathed regular air (approximately 21% $O_2$) at a normal breathing rate for a period of 4 minutes (up to approximately 240 seconds). At t=4 minutes, the individual was placed on hypoxic air of 5% oxygen (5% $O_2$, 95% $N_2$). After 2 minutes of breathing the hypoxic mix (120 seconds), the individual was administered one breath of a 13% oxygen mix (13% $O_2$, 87% $N_2$) and then immediately returned to the hypoxic 5% $O_2$ mix for an additional 2 minutes. At the 8 minutes mark (480 seconds), the individual was returned to normal air (approximately 21% $O_2$).

During the test, the individual wore the broad-spectrum oximeter as described herein on their head, in parallel to the conventional cerebral oximeter. FIG. 17 shows the measurements obtained by the conventional cerebral oximeter, which outputs regional saturation (RSO2) values in percentages (line 1702), as compared to the index calculated by the broad-spectrum oximeter of the present disclosure (line 1704), as described above, over time in seconds. Line 1702 thus shows the RSO2 measured with the conventional regional oximeter, and line 1704 shows an index calculated from the broad range spectral data acquired by the broad-spectrum oximeter of the present disclosure. In line 1704, as mentioned, the index used is a simple ratio of the AUC from the wavelengths above and below 800 nm taken by the broad-spectrum oximeter. This index allows, therefore, comparison of the results obtained by the broad-spectrum oximeter of the present disclosure with the conventional regional oximetry device (i.e. cerebral oximeter). By observing the plots based on knowledge of the test conditions described above, it is evident that delivery of the small oxygen bolus to the cerebral region is detected by the broad-spectrum oximeter of the present disclosure—line 1704 clearly indicates a small peak between 300 and 400 seconds. In contrast, the data of the conventional regional oximetry device, line 1702, reflects a relatively stable curve, with a general decreasing trend or lag. Thus, line 1702 in no way reflects delivery of the small oxygen bolus to the cerebral region, despite the conventional regional oximetry device being well-established and a standard in the field. It is therefore evident from the comparative readings that the small increase in $O_2$ level at the cerebral region was only registered by the broad-spectrum oximeter of the present disclosure (spectroximeter). As described elsewhere, the spectral resolution achievable by the broad-spectrum oximeter of the present disclosure, which can provide individual bolus detection, may be particularly useful in life-threatening scenarios.

Figure 18:
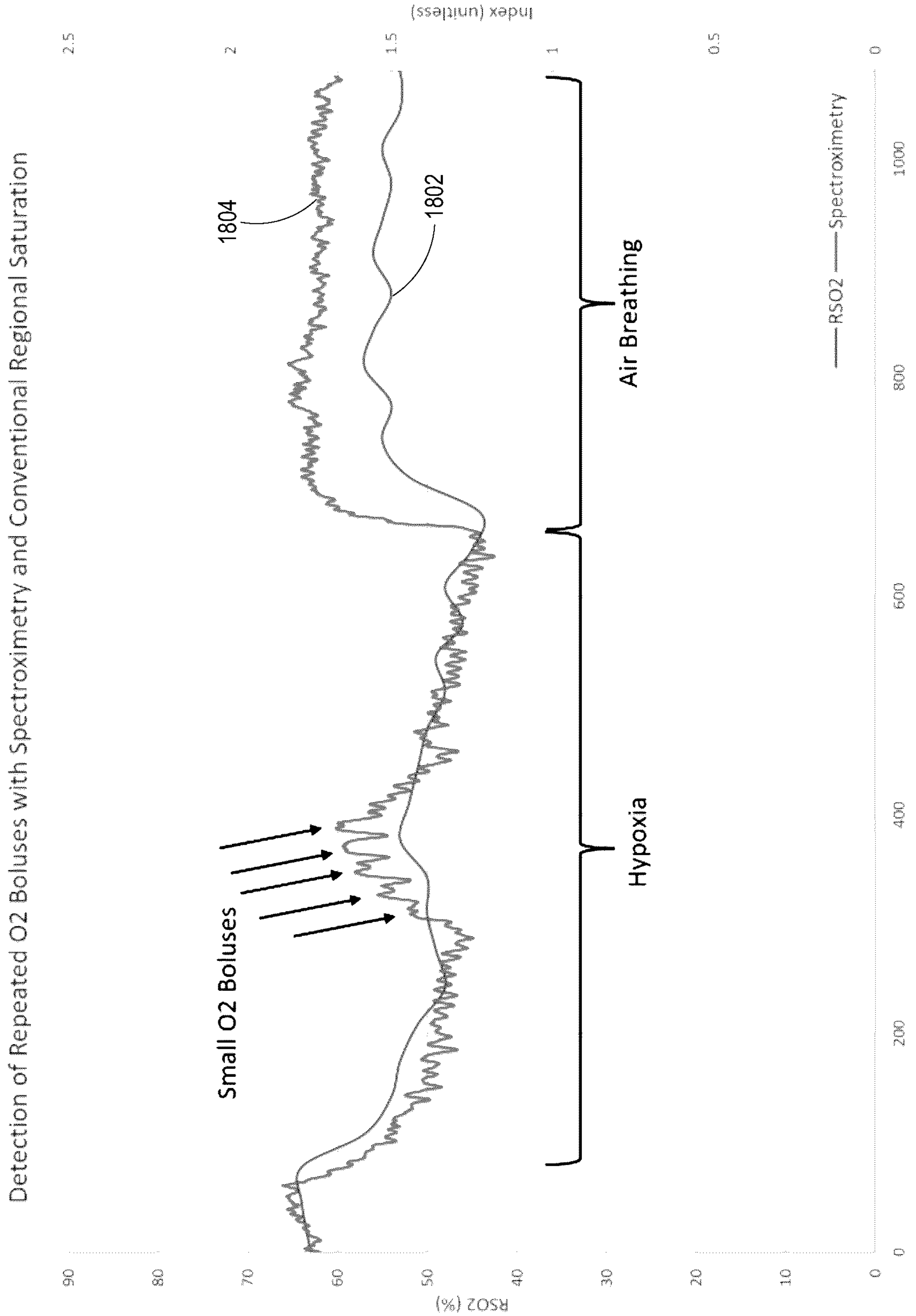
FIG. 18 is an exemplary plot of data which compares, in another test, a conventional regional oximeter (which outputs regional saturation data) with an exemplary broad-spectrum oximetry device (where output was defined, for exemplary purposes only, as an index calculated based on the area under the curve (AUC) from wavelengths above and below 800 nm), in accordance with one embodiment of the present disclosure, respectively tested to detect delivery of repeated oxygen boluses of higher oxygen concentration to an individual in a hypoxic condition, which illustrates, for example, that the resolution obtainable with the broad-spectrum oximetry device of the present disclosure is superior to the resolution obtainable by conventional regional oximeters under the same test conditions.

With reference now to FIG. 18, and in accordance with one embodiment, comparative results were obtained using a broad-spectrum oximeter as described herein (i.e. spectroximetry), and a conventional regional oximeter. Once again, in this particular embodiment, the broad-spectrum oximeter obtained and/or resolved all wavelengths in a range of 600 nm to 100 nm (not just a select few). These comparative results, taken during a single test, illustrate the improved resolution offered by the broad-spectrum oximeter as described herein, relative to conventional regional oximeters, particularly in real-time detection of boluses over time.

In the test reflected in FIG. 18, the individual was exposed to the same conditions as in the test conducted with reference to FIG. 17, with one purpose being to compare the detection of the introduction of repeated small boluses of higher $O_2$ concentrations. The test conditions were further selected to simulate closely-spaced assisted breathes and chest compressions as typically delivered during CPR.

Initially, the individual inhaled normal air (approximately 21% $O_2$). At t=1 minute, the individual began breathing a hypoxic mix of 5% $O_2$, 95% $N_2$. At t=5 minutes, the breathing was alternated between one breath of 13% $O_2$ and 5% $O_2$, with each combined inhale/exhale lasting approximately 10 seconds. A total of 5 closely-spaced breathes of 13% $O_2$ were thus administered between t=300 seconds and t=390 seconds. A return to 5% $O_2$ was performed after the 5th breath of 13% $O_2$ for another 4.5 minutes, after which the individual was returned to breathing normal air.

FIG. 18 shows the results of the measurements taken by both devices worn by the individual in parallel during the test, wherein line 1802 reflects regional saturation (RSO2) measurements outputted by the conventional regional oximeter and line 1804 reflects an AUC index derived from the broad-spectrum oximeter as described herein. In particular, the AUC index was again based on the wavelengths above 800 nm (i.e. 800 or 801 nm to 1000 nm) to those under 800 nm (i.e. 600 nm to 799 nm or 800 nm). This 2-value ratio was used for comparison purposes only, and as mentioned, more complex indices based on the high resolution wavelengths fall within the scope of the present disclosure. From the graph of FIG. 18, it can be observed that the conventional regional oximeter (i.e. cerebral monitor) can detect the overall increased trend in oxygenation during the repeated breaths of increased $O_2$ content. However, the trend is not very marked or distinct, and is delayed compared to the onset of the small boluses. In contrast, that data obtained by the broad-spectrum oximeter as described herein shows a very quick response in detection and a resolution which allows the detection of each individual small bolus, even as resulting from each breath of 13% $O_2$. Therefore, not only does the broad-spectrum oximeter as described herein offer improved resolution over existing oximetry devices, but it allows for the detection of even minute boluses which may be relevant in life-threatening scenarios. Line 1804 also illustrates the features (i.e. peaks and troughs) visible in the output from the digital data processor, which temporally correspond to discrete physiological events.

Therefore, based on all of the exemplary embodiments provided herewith, it may become apparent that the use of more distinct spectral responses (specifically more than two, in some embodiments 10, 40 or 80) by system 100 in the index calculation may significantly increase the sensitivity and detectability of oxygen bolus events, both increases and decreases, making broad range measurements much faster and more sensitive to detect small increases or decreases of oxygen. Nonetheless, embodiments as considered herein are not limited to broad-spectrum solution, as noted above, and as exemplified by the processing results described herein.

Furthermore, as illustrated, the system 100 in this embodiment is capable of detecting events of increased oxygen at the cerebral region due to inhalation. It may be extrapolated that increased oxygen due to chest compressions administered during CPR, for example, would similarly be detectable and thus system 100 may be utilised to analyse the efficacy of CPR on a patient in real time or otherwise, to provide real-time feedback on the technique of a CPR trainee. In this regard, one major drawback of conventional pulse oximeters in the context of cardiac arrest is that such pulse oximeters require a (detectable) pulse to derive accurate blood oxygen measurements, as described above. As a result, for example, an emergency responder typically administers CPR to a user in cardiac arrest without knowledge of oxygen levels at the brain and/or efficacy of their CPR administration. System 100 may provide real time oxygen level variations with sufficient temporal resolution to allow the emergency responder to observe each rescue breath or compression administered, thus allowing observation of efficacy of CPR, predict user outcome and/or adjust CPR technique based on oxygen levels at the brain. In one anecdotal example, where an emergency responder is administering CPR to a patient, the emergency responder may be inclined to cease chest compressions due to fracturing one or more ribs of the patient. In this scenario, utilising system 100 to obtain real time temporal variations reflecting oxygen delivery at the user body region may indicate to the emergency responder the efficacy of the chest compressions in delivering oxygen to the user body region and thus encourage continued administering of chest compressions despite the rib fracture.

Other findings based on the accurate, real time data obtained by system 100 will be readily conceivable by skilled technicians. For example, returning to the index plot in FIG. 11, one can observe that the decrease in oxygen levels after the first large oxygen bolus (i.e. after 4 minutes) did not decline to the level before the inhalation. Thus, although the initial $O_2$ consumption at the specific site was likely high, thereafter the overall oxygen level was left comparatively higher than prior to the large oxygen bolus. One can observe further that the second large bolus at 8 minutes did not result in an oxygen level increase as significant as the first large oxygen bolus, despite each bolus comprising 100% $O_2$. Similar findings and determinations based on the real time data from system 100 can be considered without departing from the general scope and nature of the present disclosure.

Furthermore, the system 100 appears to be more sensitive to temporal variations caused due to oxygen boluses at the cerebral region as compared to temporal variations at the wrist region or other extremities.

The nature of system 100 further allows specifically for the temporal measurement and/or monitoring of oxygen levels in a user body region. Therefore, an oxygen transport time between delivery or administering of oxygen to a user (by inhalation, intubation, CPR or otherwise) and arrival of oxygen at a user body region for consumption can be determined. For example, referring back to FIG. 11, the time required for an oxygen bolus to travel from the lungs to the cerebral region can be derived by properly timing the time between the inhalation and the measured increase in $O_2$ by system 100. This transport time may be correlated to blood pressure, other factors such as $O_2$ inhalation capacity, and yet further factors which will be appreciable by skilled technicians. The use of a large oxygen bolus allows a clearer determination of the inflection point which would be indicative of the onset of $O_2$ increase. As system 100 can be utilized at various user body regions, oxygen transport time can be determined at other regions of the body, which may be relevant, as examples, after an injury to a particular region or in assessing sports performance.

It is to be appreciated that in some embodiments, other long-term trends may be obtainable from system 100 and the real time temporal variations monitored. For example, temporal variations identified by system 100 may be evaluated by a machine learning algorithm to identify long-term trends.

It is to be appreciated further that in some embodiments, temporal variations monitored by system 100 may inform treatment of a user. For example, an increased oxygen concentration may be administered to a user when system 100 identifies temporal variations and specifically, a high oxygen transport time, associated with low pulmonary oxygen diffusion or uptake.

In some embodiments, system 100 therefore provides for hyperspectral oximetry and associated medical applications.

In accordance with yet a further aspect of the disclosure, there is provided a non-transitory computer-readable medium comprising instructions to be implemented by a digital data processor to temporally monitor oxygen levels at a user body region in real time, by: activating a light source providing illumination within a designated spectral region to the user body region to probe various blood-borne chromophores exhibiting respective spectral responses within the designated spectral region, acquiring from a spectrometer an optical signal from the user body region resulting from the illumination so to digitally capture a response including the respective spectral responses, and processing, via a digital data processor, the response in real time to automatically identify temporal variations therein representative of oxygen delivery variations at the user body region, wherein the processing achieves a resolution of the temporal variations allowing individual physiological event identification in real time.

Again, in this example, the light source is a broad-spectrum light source which provides broad-spectrum illumination. Accordingly, the response is a broad-spectrum response.

Skilled technicians will understand this aspect of the disclosure to relate, for example, to the software at least partially enabling system 100. The non-transitory computer-readable medium thus may include instructions directed to each of the features potentially forming part of system 100, as described, as well as additional or complementary features which will be readily conceivable by skilled technicians based on the present disclosure.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A system for interfacing with a user body region to monitor a physiological condition, the system comprising:

a broad-spectrum light source providing broad-spectrum illumination to the user body region within a designated spectral region to probe multiple blood-borne chromophores associated with the physiological condition and exhibiting respective spectral responses within said designated spectral region;

a spectrometer operable to acquire an optical signal from the user body region resulting from said broad-spectrum illumination so to digitally capture a broad-spectrum response encompassing said respective spectral responses; and a digital data processor which processes respective spectral wavelength regions of said broad-spectrum response to at least partially spectrally resolve said respective spectral responses for at least two of said blood-borne chromophores to output a health-related indicator associated with a relative concentration of said at least two blood-borne chromophores representative of the physiological condition.

2. The system of claim 1, wherein the physiological condition comprises a physiological event, and wherein said digital data processor is operable to process said broad-spectrum response in real time so to output a temporally variable health-related indicator that temporally resolves the physiological event.

3. The system of claim 1, wherein said digital data processor is further operable to spectrally resolve said respective spectral responses to isolate respective spectral signatures for said at least two of said blood-borne chromophores and compare said signatures with designated signatures associated with a discriminable physiological condition to output said health-related indicator.

4. The system of claim 1, wherein said digital data processor is further operable to spectrally resolve said respective spectral responses to isolate respective spectral signatures for at least one of said blood-borne chromophores, and wherein said digital data processor is operable to extract respective absolute concentrations for said at least one of said blood-borne chromophores from said respective spectral signatures.

5. The system of claim 3, wherein said digital data processor is operable to: process a combined spectral signature associated with said at least two blood-borne chromophores and to compare said combined spectral signature with a designated set of corresponding signatures to characterize an extent of said physiological condition via said health-related indicator.

6. The system of claim 3, wherein said digital data processor is operable to extract a variation in said spectral signatures over time and compare said variation with said designated signatures to output said health-related indicator.

7. The system of claim 1, wherein said broad-spectrum light source comprises a full spectrum infrared (IR) light source.

8. The system of claim 1, wherein said broad-spectrum light source emits light in a range of about 600 nm to about 1000 nm.

9. The system of claim 1, wherein said spectrometer is operable to isolate respective spectral responses within at least 10 spectral regions within said broad-spectrum illumination.

10. The system of claim 1, wherein said spectrometer is operable to isolate respective spectral responses within at least 40 spectral regions within said broad-spectrum illumination.

11. The system of claim 1, wherein said spectrometer is operable to isolate respective spectral responses within at least 80 spectral regions within said broad-spectrum illumination.

12. The system of claim 9, wherein said digital data processor is operable to identify overlapping respective spectral responses in said optical signal by deconstructing said optical signal via spectral deconvolution.

13. The system of claim 1, wherein said user body region comprises a cerebral region, and wherein said broad-spectrum light source and spectrometer are integrated within a headband.

14. The system of claim 1, wherein said digital data processor is operable to output a time-variable integrated response amplitude, and wherein temporal variations of said respective spectral responses are reflected as temporally corresponding features in said time-variable integrated response amplitude.

15. The system of claim 14, wherein said digital data processor is operable to derive from said time-variable integrated response amplitude a temporal index representative of said respective spectral responses, and wherein said temporal index has a resolution sufficient to observe said temporal variations in said respective spectral responses corresponding to discrete physiological events over time.

16. The system of claim 1, wherein said blood-borne chromophores comprise water molecules and wherein the system is further configured to monitor hydration levels at the user body region based on temporal variations of said water molecules.

17. The system of claim 1, wherein said digital data processor is operable to store said broad-spectrum response on a memory to configure a user-specific spectral index, wherein said digital data processor is operable to compare said broad-spectrum response with said user-specific spectral index to predict a user outcome based on temporal variations therebetween.

18. The system of claim 1, wherein the physiological condition comprises oxygen delivery to the user body region, wherein said blood-borne chromophores comprise at least one blood-oxygenation-related chromophore, wherein said digital data processor is operable to digitally resolve oxygen delivery variations over time based on variations in said at least one blood-oxygenation-related chromophore to digitally identify any one of: an oxygen concentration increase, an oxygen concentration decrease, or a relatively unchanged oxygen concentration, which is temporally associated with one or more physiological events experienced by the user.

19. The system of claim 18, wherein said one or more physiological events resulting in said oxygen concentration increase comprise any one or combination of: inhalation by the user; intubation of the user; or mechanical administration of cardiopulmonary resuscitation (CPR) to the user.

20. The system of claim 18, wherein said one or more physiological events resulting in said oxygen concentration decrease comprise any one or combination of: an obstructed airway of the user; sleep apnea of the user; or cardiac arrest of the user.

* * * * *